United States Patent
Probst et al.

(12)

(10) Patent No.: US 6,447,779 B1
(45) Date of Patent: Sep. 10, 2002

(54) COMPOUNDS FOR THE DIAGNOSIS OF CHLAMYDIAL INFECTION

(75) Inventors: Peter Probst; Ajay Bhatia; Yasir A. W. Skeiky, all of Seattle; Steven P. Fling, Bainbridge Island, all of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/288,594

(22) Filed: Apr. 8, 1999

Related U.S. Application Data

(63) Continuation-in-part of application No. 09/208,277, filed on Dec. 8, 1998, now Pat. No. 6,166,177.

(51) Int. Cl.[7] .................. A61K 39/02; A61K 39/00; A61K 39/38; A61K 39/385
(52) U.S. Cl. ............... 424/190.1; 424/184.1; 424/192.1; 424/197.11
(58) Field of Search ............... 424/184.1, 190.1, 424/192.1, 197.11, 200.1; 436/512; 530/300, 388.4

(56) References Cited

U.S. PATENT DOCUMENTS

| | | | |
|---|---|---|---|
| 4,118,469 A | 10/1978 | Caldwell et al. ............... 424/1 |
| 4,497,899 A | * 2/1985 | Armstrong et al. ......... 436/510 |
| 5,166,053 A | * 11/1992 | Huguenel et al. .......... 435/7.36 |
| 5,318,892 A | 6/1994 | Watanabe et al. .......... 435/7.36 |
| 5,725,863 A | * 3/1998 | Daniels et al. ........... 424/263.1 |

FOREIGN PATENT DOCUMENTS

| | | |
|---|---|---|
| EP | 0784 059 A | 7/1997 |
| WO | WO 98/02546 | 1/1998 |
| WO | WO 98/10789 | 3/1998 |
| WO | WO 97/06263 | 2/1999 |
| WO | WO 99/27105 | 6/1999 |
| WO | WO 99/28475 | 6/1999 |
| WO | WO 99/51748 | 10/1999 |
| WO | WO 00/34483 | 6/2000 |

OTHER PUBLICATIONS

Levinson et.al.; Medical Microbiology & Immunology, 1994,Immunity: 292–293.*
Rank et al, Infect. and Immun., 58(8): 2599–605, 1990.*
Stephens et al. GenCore Accession No. AE001320, AE01335, AE001273, AE001323, AE001324, AE001326, AE001316, Sep. 1998.*
Stephens et al. GenCore Accession No. E71500, H71501, H71510, Sep. 1998.*
Baehr et al., "Mapping antigenic domains expressed by chlamydia trachomatis major outer membrane protein genes," *Proc Natl Acad Sci* 85(1):4000–4004, Jun. 1, 1988.
Brunham et al., "Chlamydia trachomatis antigens: role in immunity and pathogenesis," *Infectious Agents and Disease* 3(5):218–233, Oct. 1994.
Genbank Accession No. AE001361, Jul. 22, 1998.
Genbank Accession No. AE001316, Dec. 13, 1999.
Genbank Accession No. AE001320, Dec. 13, 1999.
Genbank Accession No. AE001326, Dec. 13, 1999.
Gu et al., "Chlamydia trachomatis RNA Polymerase α Subunit: Sequence and Structural Analysis." *J. Bacteriology* 177(9):2594–2601, 1995.
Sanderson et al., "Indentification of a CD4[+] T Cell–stimulating Antigen of Pathogenic Bacteria by Expression Cloning," *J. Exp. Med.* 182(6):1751–1757, 1995.
Scudiero et al., "Evaluation of a Soluble Tetrazolium/Formazan for Cell Growth and Drug Sensitivity in Culture Using Human and Other Tumor Cell Lines," *Cancer Research* 48(17):4827–4833, 1988.
Stephens et al., "Genome Sequence of an Obligate Intracellular Pathogen of Humans: *Chlamydia trachomatis*," *Science* 282:754–759, 1998.

* cited by examiner

*Primary Examiner*—Deborah Crouch
*Assistant Examiner*—Joseph Woitach
(74) *Attorney, Agent, or Firm*—Seed Intellectual Property Law Group PLLC

(57) ABSTRACT

Compounds and methods for the diagnosis and treatment of Chlamydial infection are disclosed. The compounds provided include polypeptides that contain at least one antigenic portion of a Chlamydia antigen and DNA sequences encoding such polypeptides. Pharmaceutical compositions and vaccines comprising such polypeptides or DNA sequences are also provided, together with antibodies directed against such polypeptides. Diagnostic kits containing such polypeptides or DNA sequences and a suitable detection reagent may be used for the detection of Chlamydial infection in patients and in biological samples.

14 Claims, 7 Drawing Sheets

CP SWIB Nde (5' primer)
5' GATATACATATGCATCACCATCACCATCACATGAGTCAAAAAAATAAAAACTCT CP SWIB EcoRI (3' primer)
5' CTCGAGGAATTCTTATTTTACAATATGTTTGGA CP S13 Nde (5' primer)
5' GATATACATATGCATCACCATCACCATCACATGCCACGCATCATTGGAATGAT CP S13 EcoRI (3' primer)
5' CTCGAGGAATTCTTATTTCTTCTTACCTGC

*Fig. 6*

COMPOUNDS FOR THE DIAGNOSIS OF CHLAMYDIAL INFECTION

REFERENCE TO RELATED APPLICATIONS

This application is a continuation-in-part of U.S. patent application No. 09/208,277, filed Dec. 8, 1998 now U.S. Pat. No. 6,166,177.

TECHNICAL FIELD

The present invention relates generally to the detection and treatment of Chiamydial infection. In particular, the invention is related to polypeptides comprising a Chlamydia antigen and the use of such polypeptides for the serodiagnosis and treatment of Chlamydial infection.

BACKGROUND OF THE INVENTION

Chlamydiae are intracellular bacterial pathogens that are responsible for a wide variety of important human and animal infections. *Chlamydia trachomatis* is one of the most common causes of sexually transmitted diseases and can lead to pelvic inflammatory disease (PID), resulting in tubal obstruction and infertility. *Chlamydia trachomatis* may also play a role in male infertility. In 1990, the cost of treating PID in the US was estimated to be $4 billion. Trachoma, due to ocular infection with *Chlamydia trachomatis*, is the leading cause of preventable blindness worldwide. *Chlamydia pneumonia* is a major cause of acute respiratory tract infections in humans and is also believed to play a role in the pathogenesis of atherosclerosis and, in particular, coronary heart disease. Individuals with a high titer of antibodies to *Chlamydia pneumonia* have been shown to be at least twice as likely to suffer from coronary heart disease as seronegative individuals. Chlamydial infections thus constitute a significant health problem both in the US and worldwide.

Chlamydial infection is often asymptomatic. For example, by the time a woman seeks medical attention for PID, irreversible damage may have already occurred resulting in infertility. There thus remains a need in the art for improved vaccines and pharmaceutical compositions for the prevention and treatment of Chlamydia infections. The present invention fulfills this need and further provides other related advantages.

SUMMARY OF THE INVENTION

The present invention provides compositions and methods for the diagnosis and treatment of Chlamydia infection. In one aspect, polypeptides are. provided comprising an immunogenic portion of a Chlamydia antigen, or a variant of such an antigen. In one embodiment, the antigen comprises an amino acid sequence encoded by a DNA sequence selected from the group consisting of (a) a sequence of SEQ ID NO: 1, 15 or 21–25; (b) the complements of said sequences; and (c) sequences that hybridize to a sequence of (a) or (b) under moderately stringent conditions. In a specific embodiment, a polypeptide comprising an amino acid sequence of SEQ ID NO: 5 is provided.

In a related aspect, polynucleotide sequences encoding the above polypeptides, recombinant expression vectors comprising one or more of these polynucleotide sequences and host cells transformed or transfected with such expression vectors are also provided.

In another aspect, the present invention provides fusion proteins comprising an inventive polypeptide, or, alternatively, an inventive polypeptide and a known Chlamydia antigen. In yet another aspect, the present invention provides antibodies, both polyclonal and monoclonal, that bind to the polypeptides described. above.

Within other aspects, the present invention provides pharmaceutical compositions that comprise one or more Chlamydia polypeptides disclosed herein, or a polynucleotide molecule encoding such polypeptides, and a physiologically acceptable carrier. The invention also provides vaccines comprising one or more of the disclosed polypeptides and a non-specific immune response enhancer, together with vaccines comprising one or more polynucleotide sequences encoding such polypeptides and a non-specific immune response enhancer.

In yet another aspect, methods are provided for inducing protective immunity in a patient, comprising administering to a patient an effective amount of one or more of the above pharmaceutical compositions or vaccines.

In yet a further aspect, methods for the treatment of Chlamydia infection in a patient are provided, the methods comprising obtaining PBMC from the patient, incubating the PBMC with a polypeptide of the present invention (or a polynucleotide that encodes such a polypeptide) to provide incubated T cells and administering the incubated T cells to the patient. The present invention additionally, provides methods for the treatment of Chlamydia infection that comprise incubating antigen presenting cells with a polypeptide of the present invention (or a polynucleotide that encodes such a polypeptide) to provide incubated antigen presenting cells and administering the incubated antigen presenting cells to the patient. In certain embodiments, the antigen presenting cells are selected from the group consisting of dendritic cells, macrophages, monocytes, B-cells, and fibroblasts. Compositions for the treatment of Chlamydia infection comprising T cells or antigen presenting cells that have been incubated with a polypeptide or polynucleotide of the present invention are also provided.

In further aspects of the subject invention, methods and diagnostic kits are provided for detecting Chlamydia infection in a patient. In one embodiment, the method comprises: (a) contacting a biological sample with at least one of the polypeptides or fusion proteins disclosed herein; and (b) detecting in the sample the presence of antibodies that bind to the polypeptide or fusion protein, thereby detecting Chlamydia infection in the biological sample. Suitable biological samples include whole blood, sputum, serum, plasma, saliva, cerebrospinal fluid and urine. In one embodiment, the diagnostic kits comprise one or more of the polypeptides or fusion proteins disclosed herein in combination with a detection reagent. In yet another embodiment, the diagnostic kits comprise either a monoclonal antibody or a polyclonal antibody that binds with a polypeptide of the present invention.

The present invention also provides methods for detecting Chlamydia infection comprising: (a) obtaining a biological sample from a patient; (b) contacting the sample with at least two oligonucleotide primers in a polymerase chain reaction, at least one of the oligonucleotide primers being specific for a polynucleotide sequence disclosed herein; and (c) detecting in the sample a polynucleotide sequence that amplifies in the presence of the oligonucleotide primers. In one embodiment, the oligonucleotide primer comprises at least about 10 contiguous nucleotides of a polynucleotide sequence eptide disclosed herein, or of a sequence that hybridizes thereto.

In a further aspect, the present invention provides a method for detecting Chlamydia infection in a patient comprising: (a) obtaining a biological sample from the patient;

(b) contacting the sample with an oligonucleotide probe specific for a polynucleotide sequence disclosed herein; and (c) detecting in the sample a polynucleotide sequence that hybridizes to the oligonucleotide probe. In one embodiment, the oligonucleotide probe comprises at least about 15 contiguous nucleotides of a polynucleotide sequence disclosed herein, or a sequence that hybridizes thereto.

These and other aspects of the present invention will become apparent upon reference to the following detailed description. All references disclosed herein are hereby incorporated by reference in their entirety as if each was incorporated individually.

SEQUENCE IDENTIFIERS

SEQ ID NO: 1 is the determined DNA sequence for the *C. trachomatis* clone 1-B1-66.

SEQ ID NO: 2 is the determined DNA sequence for the *C. trachomatis* clone 4-D7-28.

SEQ ID NO: 3 is the determined DNA sequence for the *C. trachomatis* clone 3-G3-10.

SEQ ID NO: 4 is the determined DNA sequence for the *C. trachomatis* clone 10-C10-31.

SEQ ID NO: 5 is the predicted amino acid sequence for 1-B1-66.

SEQ ID NO: 6 is the predicted amino acid sequence for 4-D7-28.

SEQ ID NO: 7 is a first predicted amino acid sequence for 3-G3-10.

SEQ ID NO: 8 is a second predicted amino acid sequence for 3-G3-10.

SEQ ID NO: 9 is a third predicted amino acid sequence for 3-G3-10.

SEQ ID NO: 10 is a fourth predicted amino acid sequence for 3-G3-10.

SEQ ID NO:11 is a fifth predicted amino acid sequence for 3-G3-10.

SEQ ID NO: 12 is the predicted amino acid sequence for 10-C10-31.

SEQ ID NO: 13 is the amino acid sequence of the synthetic peptide 1-B1-66/49-67.

SEQ ID NO: 14 is the amino acid sequence of the synthetic peptide 1-B1-66/58-77.

SEQ ID NO: 15 is the determined DNA sequence for the *C. trachomatis* serovar LGV II clone 2C7-8.

SEQ ID NO: 16 is the determined DNA sequence for a first putative open reading frame from *C. trachomatis* serovar D.

SEQ ID NO: 17 is the predicted amino acid sequence encoded by the first putative open reading frame from *C. trachomatis* serovar D.

SEQ ID NO: 18 is the determined amino acid sequence of the synthetic peptide CtC7.8-12.

SEQ ID NO: 19 is the determined amino acid sequence of the synthetic peptide CtC7.8-13.

SEQ ID NO: 20 is the predicted amino acid sequence encoded by a second putative open reading from *C. trachomatis* serovar D.

SEQ ID NO: 21 is the determined DNA sequence for clone 4C9-18 from *C. trachomatis* LGV II.

SEQ ID NO: 22 is the determined DNA sequence homologous to Lipoamide Dehydrogenase from *C. trachomatis* LGV II.

SEQ ID NO: 23 is the determined DNA sequence homologous to Hypothetical protein from *C. trachomatis* LGV II.

SEQ ID NO: 24 is the determined DNA sequence homologous to Ubiquinone Mehtyltransferase from *C. trachomatis* LGV II.

SEQ ID NO: 25 is the determined DNA sequence for clone 4C9-18#2 BL21 pLysS from *C. trachomatis* LGV II.

SEQ ID NO: 26 is the predicted amino acid sequence for 4C9-18#2 from *C. trachomatis LGV II*.

SEQ ID NO: 27 is the determined DNA sequence for Cp-SWIB from *C. pneumonia* strain TWAR.

SEQ ID NO: 28 is the predicted amino acid sequence for Cp-SWIB from *C. pneumonia* strain TWAR.

SEQ ID NO: 29 is the determined DNA sequence for Cp-S13 from *C. pneumonia* strain TWAR.

SEQ ID NO: 30 is the predicted amino acid sequence for Cp-S13 from *C. pneumonia* strain TWAR.

SEQ ID NO: 31 is the amino acid sequence for a 10 mer consensus peptide from CtC7.8-12 and CtC7.8-13.

SEQ ID NO: 32 is the predicted amino acid sequence for clone 2C7-8 from *C. trachomatis* LGV II.

SEQ ID NO: 33 is the determined DNA sequence of a clone from *C. trachomatis* serovar D which shows homology to clone 2C7-8.

SEQ ID NO: 34 is the predicted amino acid sequence encoded by the sequence of SEQ ID NO: 33.

SEQ ID NO: 35 is the determined DNA sequence for C.p. SWIB Nde (5' primer) from *C. pneumonia*.

SEQ ID NO: 36 is the determined DNA sequence for C.p. SWIB EcoRI (3' primer) from *C. pneumonia*.

SEQ ID NO: 37 is the determined DNA sequence for C.p. S13 Nde (5' primer) from *C. pneumonia*.

SEQ ID NO: 38 is the determined DNA sequence for C.p. S13 EcoRI (3' primer) *C. pneumonia*.

DESCRIPTION OF THE FIGURES

FIG. 6 illustrates the 5' and 3' primer sequences designed from *C. pnuemonia* which were used to isolate the SWIB and S13 genes from *C. pnuemonia*.

DETAILED DESCRIPTION OF THE INVENTION

Figure 1:
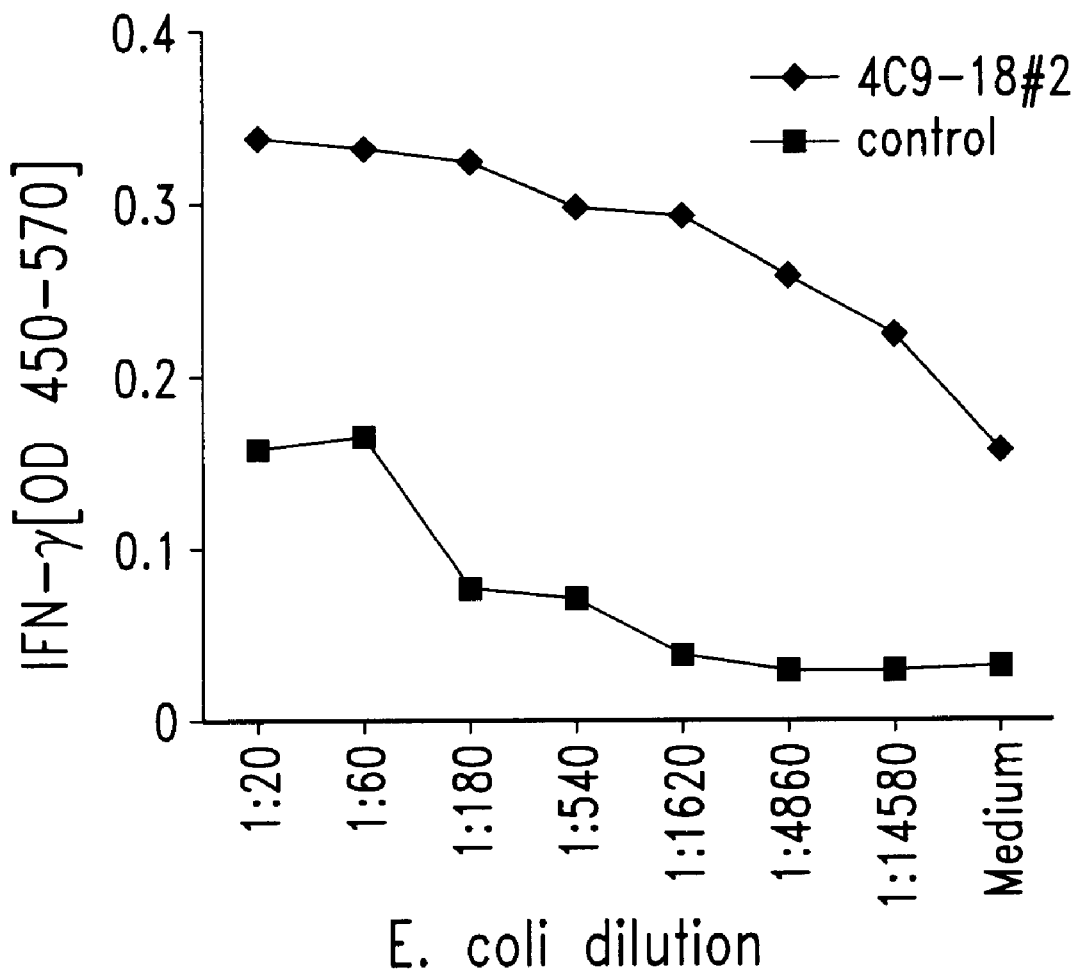
FIG. 1 illustrates induction of INF-γ from a Chlamydia-specific T cell line activated by target cells expressing clone 4C9-18#2.

As noted above, the present invention is generally directed to compositions and methods for the diagnosis and treatment of Chlamydial infection. In one aspect, the compositions of the subject invention include polypeptides that comprise at least one immunogenic portion of a Chlamydia antigen, or a variant thereof.

In specific embodiments, the subject invention discloses polypeptides comprising an immunogenic portion of a Chlamydia antigen, wherein the Chlamydia antigen comprises an amino acid sequence encoded by a polynucleotide molecule including a sequence selected from the group consisting of (a) nucleotide sequences recited in SEQ ID NO: 1–4, 15 and 21–25 (b) the complements of said nucleotide sequences, and (c) variants of such sequences.

As used herein, the term "polypeptide" encompasses amino acid chains of any length. including full length proteins (i.e., antigens), wherein the amino acid residues are linked by covalent peptide bonds. Thus, a polypeptide comprising an immunogenic portion of one of the inventive antigens may consist entirely of the immunogenic portion, or may contain additional sequences. The additional sequences may be derived from the native Chlamydia antigen or may be heterologous, and such sequences may (but need not) be immunogenic.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

An "immunogenic portion" of an antigen is a portion that is capable of reacting with sera obtained from a Chlamydia-infected individual (i.e., generates an absorbance reading with sera from infected individuals that is at least three standard deviations above the absorbance obtained with sera from uninfected individuals, in a representative ELISA assay described herein). Such immunogenic portions generally comprise at least about 5 amino acid residues, more preferably at least about 10, and most preferably at least about 20 amino acid residues. Methods for preparing and identifying immunogenic portions of antigens of known sequence are well known in the art and include those summarized in Paul, *Fundamental Immunology*, $3^{rd}$ ed., Raven Press, 1993, pp. 243–247. Examples of immunogenic portions of antigens. contemplated by the present invention include, for example, the T cell stimulating epitopes provided in SEQ ID NO: 9, 10, 18. 19, 31 and 39. Polypeptides comprising at least an immunogenic portion of one or more Chlamydia antigens as described herein may generally be used, alone or in combination, to detect Chlamydial infection in a patient.

The compositions and methods of the present invention also encompass variants of the above polypeptides and polynucleotide molecules. Such variants include, but are not limited to, naturally occurring allelic variants of the inventive sequences.

A polypeptide "variant," as used herein, is a polypeptide that differs from the recited polypeptide only in conservative substitutions and/or modifications, such that the antigenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. Polypeptide variants preferably exhibit at least about 70%, more preferably at least about 90% and most preferably at least about 95% identity (determined as describe below) to the identified polypeptides.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants as discussed below. or non-naturally occurring variants. Variant nucleotide sequences preferably exhibit at least about 70%, more preferably at least about 80% and most preferably at least about 90% identity (determined as described below) to the recited sequence.

The Chlamydia antigens provided by the present invention include variants that are encoded by polynucleotide sequences which are substantially homologous to one or more of the polynucleotide sequences specifically recited herein. "Substantial homology," as used herein, refers to polynucleotide sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.–65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing polynucleotide sequences are also within the scope of this invention, as are nucleotide sequences that, due to code degeneracy, encode an immunogenic polypeptide that is encoded by a hybridizing polynucleotide sequence.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Resarch Foundaiton, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer *CABIOS* 5:151–153; Myers, E. W. and Muller W. (1988) Optimal alignments in linear space *CABIOS* 4:11–17; Robinson, E. D. (1971) *Comb. Theor* 11:105; Santou, N. Nes, M. (1987) The neighbor joining method. A new method for reconstructing phylogenetic trees *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) Rapid similarity searches of nucleic acid and protein data banks *Proc. Natl. Acad, Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions. dividing the number of matched positions by the total number of positions in the reference sequence (i.e. the window size) and multiplying the results by 100 to yield the percentage of sequence identity. Also included in the scope of the present invention are alleles of the genes encoding the nucleotide sequences recited in herein. As used herein, an "allele" or "allellic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone or in combination with the others, one or more times in a given sequence. In specific embodiments, the subject invention discloses polypeptides comprising at least an immunogenic portion of a Chlamydia antigen (or a variant of such an antigen), that comprises one or more of the amino acid sequences encoded by (a) a polynucleotide sequence selected from the group consisting of SEQ ID NO: 1–4, 15 and 21–25(b) the complements of such DNA sequences or (c) DNA sequences substantially homologous to a sequence in (a) or (b). As discussed in the Examples below, several of the Chlamydia antigens disclosed herein recognize a T cell line that recognizes both *Chlamydia trachomatis* and *Chlamydia pneumonia* infected monocyte-derived dendritic cells, suggesting that they may represent an immunoreactive epitope shared by *Chlamydia trachomatis* and *Chlamydia pneumonia*. The antigens may thus be employed in a vaccine for both *C. trachomatis* genital tract infections and for *C. pneumonia* infections. Further characterization of these Chlamydia antigens from *Chlamydia trachomatis* and *Chlamydia pneumonia* to determine the extent of cross-reactivity is provided in Example 6. Additionally, Example 4 describes cDNA fragments (SEQ ID NO: 15, 16 and 33) isolated from *C. trachomatis* which encode proteins (SEQ ID NO: 17–19 and 32) capable of stimulating a Chlamydia-specific murine H2-Ld restricted CD8 T cell line.

In general, Chlamydia antigens, and polynucleotide sequences encoding such antigens, may be prepared using any of a variety of procedures. For example, polynucleotide molecules encoding Chlamydia antigens may be isolated from a Chlamydia genomic or cDNA expression library by screening with a Chlamydia-specific T cell line as described below, and sequenced using techniques well known to those of skill in the art. Antigens may be produced recombinantly, as described below, by inserting a polynucleotide sequence that encodes the antigen into an expression vector and expressing the antigen in an appropriate host. Antigens may be evaluated for a desired property, such as the ability to react with sera obtained from a Chlamydia-infected individual as described herein, and may be sequenced using, for example, traditional Edman chemistry. See Edman and Berg, *Eur. J. Biochem.* 80:116–132, 1967.

Polynucleotide sequences encoding antigens may also be obtained by screening an appropriate Chlamydia cDNA or genomic DNA library for polynucleotide sequences that hybridize to degenerate oligonucleotides derived from partial amino acid sequences of isolated antigens. Degenerate oligonucleotide sequences for use in such a screen may be designed and synthesized, and the screen may be performed, as described (for example) in Sambrook et al., *Molecular Cloning: A Laboratory Manual*, Cold Spring Harbor Laboratories, Cold Spring Harbor, N.Y. (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

An amplified portion may be used to isolate a full length gene from a suitable library (e.g., a Chlamydia cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$P) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using techniques well known in the art (see, for example, Mullis et al., *Cold Spring Harbor Symp. Quant. Biol.* 51:263, 1987; Erlich ed., PCR Technology, Stockton Press, NY, 1989), and software well known in the art may also be employed. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111–19, 1991) and walking PCR (Parker et al., *Nucl. Acids. Res.* 19:3055–60, 1991). Transcription-Mediated Amplification, or TMA is another method that may be utilized for the amplification of DNA, rRNA, or mRNA, as described in Patent No. PCT/US91/03184. This autocatalytic and isothermic non-PCR based method utilizes two primers and two enzymes: RNA polymerase and reverse transcriptase. One primer contains a promoter sequence for RNA polymerase. In the first amplification, the promoter-primer hybridizes to the target rRNA at a defined site. Reverse transcriptase creates a DNA copy of the target rRNA by extension from the 3'end of the promoter-primer. The RNA in the resulting complex is degraded and a second primer binds to the DNA copy. A new strand of DNA is synthesized from the end of the primer by reverse transcriptase creating double stranded DNA. RNA polymerase recognizes the promoter sequence in the DNA template and initiates transcription. Each of the newly synthesized RNA amplicons re-enters the TMA process and serves as a template for a new round of replication leading to the expotential expansion of the RNA amplicon. Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division, Foster City, Calif., and may be operated according to the manufacturer's instructions.

As noted above, immunogenic portions of Chlamydia antigens may be prepared and identified using well known techniques, such as those summarized in Paul, *Fundamental Immunology*, 3d ed., Raven Press, 1993, pp. 243–247 and references cited therein. Such techniques include screening polypeptide portions of the native antigen for immunogenic properties. The representative ELISAs described herein may generally be employed in these screens. An immunogenic portion of a polypeptide is a portion that, within such representative assays, generates a signal in such assays that is substantially similar to that generated by the full length antigen. In other words, an immunogenic portion of a Chlamydia antigen generates at least about 20%, and preferably about 100%, of the signal induced by the full length antigen in a model ELISA as described herein.

Portions and other variants of Chlamydia antigens may be generated by synthetic or recombinant means. Variants of a native antigen may generally be prepared using standard mutagenesis techniques, such as oligonucleotide-directed site-specific mutagenesis. Sections of the polynucleotide sequence may also be removed using standard techniques to permit preparation of truncated polypeptides.

Recombinant polypeptides containing portions and/or variants of a native antigen may be readily prepared from a polynucleotide sequence encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides as described herein. Expression may be achieved in any appropriate host cell that has been transformed or transfected with an expression vector containing a polynucleotide molecule that encodes a recombinant polypeptide. Suitable host cells include prokaryotes, yeast and higher eukaryotic cells. Preferably, the host cells employed are *E. coli*, yeast or a mammalian cell line, such as COS or CHO. The DNA sequences expressed in this manner may encode naturally occurring antigens, portions of naturally occurring antigens, or other variants thereof.

In general, regardless of the method of preparation, the polypeptides disclosed herein are prepared in an isolated, substantially pure, form. Preferably, the polypeptides are at least about 80% pure, more preferably at least about 90% pure and most preferably at least about 99% pure.

In a further aspect, the present invention provides fusion proteins comprising either a first and a second inventive polypeptide, or an inventive polypeptide and a known Chlamydia antigen, together with variants of such fusion proteins. The fusion proteins of the present invention may include a linker peptide between the polypeptides.

A DNA sequence encoding a fusion protein of the present invention may be constructed using known recombinant DNA techniques to assemble separate DNA sequences encoding, for example, the first and second polypeptides, into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8562, 1986; U.S. Pat. No. 4,935,233 and U.S. Pat. No. 4,751,180. The linker sequence may be from 1 to about 50 amino acids in length. As an alternative to the use of a peptide linker sequence (when desired), one can utilize non-essential N-terminal amino acid regions (when present) on the first and second polypeptides to separate the functional domains and prevent steric hindrance.

In another aspect, the present invention provides methods for using one or more of the above polypeptides or fusion proteins (or polynucleotides encoding such polypeptides or fusion proteins) to induce protective immunity against Chlamydial infection in a patient. As used herein, a "patient" refers to any warm-blooded animal, preferably a human. A patient may be afflicted with a disease, or may be free of detectable disease and/or infection. In other words, protective immunity may be induced to prevent or treat Chiamydial infection.

In this aspect, the polypeptide, fusion protein or polynucleotide molecule is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response enhancer, such as an adjuvant or a liposome (into which the polypeptide is incorporated). Such pharmaceutical compositions and vaccines may also contain other Chlamydia antigens, either incorporated into a combination polypeptide or present within a separate polypeptide.

Alternatively, a vaccine may contain polynucleotides encoding one or more polypeptides or fusion proteins as described above, such that the polypeptide is generated in situ. In such vaccines, the polynucleotides may be present within any of a variety of delivery systems known to those of ordinary skill in the art, including nucleic acid expression systems, bacterial and viral expression systems. Appropriate nucleic acid expression systems contain the necessary polynucleotide sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the polynucleotides may be introduced using a viral expression system (e.g., vaccinia or other pox virus, retrovirus, or adenovirus), which may involve the use of a non-pathogenic (defective) virus. Techniques for incorporating polynucleotides into such expression systems are well known to those of ordinary skill in the art. The polynucleotides may also be "naked," as described, for example, in Ulmer et al., *Science* 259:1745–1749, 1993 and reviewed by Cohen, *Science* 259: 1691–1692, 1993. The uptake of naked polynucleotides may be increased by coating the polynucleotides onto biodegradable beads, which are efficiently transported into the cells.

In a related aspect, a polynucleotide vaccine as described above may be administered simultaneously with or sequentially to either a polypeptide of the present invention or a known Chlamydia antigen. For example, administration of polynucleotides encoding a polypeptide of the present invention, either "naked" or in a delivery system as described above, may be followed by administration of an antigen in order to enhance the protective immune effect of the vaccine.

Polypeptides and polynucleotides disclosed herein may also be employed in adoptive immunotherapy for the treatment of Chlamydial infection. Adoptive immunotherapy may be broadly classified into either active or passive immunotherapy. In active immunotherapy, treatment relies on the in vivo stimulation of the endogenous host immune system with the administration of immune response-modifying agents (for example, vaccines, bacterial adjuvants, and/or cytokines).

In passive immunotherapy, treatment involves the delivery of biologic reagents with established immune reactivity (such as effector cells or antibodies) that can directly or indirectly mediate anti-Chlamydia effects and does not necessarily depend on an intact host immune system. Examples of effector cells include T lymphocytes (for example, CD8+ cytotoxic T-lymphocyte, CD4+ T-helper, tumor-infiltrating lymphocytes), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage, monocyte, fibroblast, or B-cells, may be pulsed with immunoreactive polypeptides, or polynucleotide sequence(s) may be introduced into antigen presenting cells, using a variety of standard techniques well known in the art. For example, antigen presenting cells may be transfected or transduced with a polynucleotide sequence, wherein said sequence contains a promoter region appropriate for increasing expression, and can be expressed as part of a recombinant virus or other expression system. Several viral vectors may be used to transduce an antigen presenting cell, including pox virus, vaccinia virus, and adenovirus; also, antigen presenting cells may be transfected with polynucleotide sequences disclosed herein by a variety of means, including gene-gun technology, lipid-mediated delivery, electroporation, osmotic shock, and particlate delivery mechanisms, resulting in efficient and acceptable expression levels as determined by one of ordinary skill in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al. "Therapy With Cultured T Cells: Principles Revisited," *Immunological Reviews*, 157:177, 1997).

The polypeptides disclosed herein may also be employed to generate and/or isolate chlamydial-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ or CD4+ T-cell clones may be isolated from the patient, expanded using standard tissue culture techniques, and returned to the patient.

Alternatively, peptides corresponding to immunogenic portions of the polypeptides may be employed to generate chlamydia reactive T cell subsets by selective in vitro stimulation and expansion of autologous T cells to provide antigen-specific T cells which may be subsequently transferred to the patient as described, for example, by Chang et al, (*Crit. Rev. Oncol. Hematol.*, 22(3), 213, 1996). Cells of the immune system, such as T cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of antigen-specific-T cells is then expanded using standard techniques and the cells are administered back to the patient.

In other embodiments, T-cell and/or antibody receptors specific for the polypeptides disclosed herein can be cloned, expanded, and transferred into other vectors or effector cells for use in adoptive immunotherapy. In particular, T cells may be transfected with the appropriate genes to express the variable domains from chlamydia specific monoclonal antibodies as the extracellular recognition elements and joined to the T cell receptor signaling chains, resulting in T cell activation, specific lysis, and cytokine release. This enables the T cell to redirect its specificity in an MHC-independent manner. See for example, Eshhar, Z., *Cancer Immunol Immunother*, 45(3–4):131–6, 1997 and Hwu, P., et al, *Cancer Res.* 55(15):3369–73, 1995. Another embodiment may include the transfection of chlamydia antigen specific alpha and beta T cell receptor chains into alternate T cells, as in Cole, D J, et al, *Cancer Res*, 55(4):748–52, 1995.

In a further embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate disease in a murine model has been demonstrated by Cheever et al, *Immunological Reviews*, 157:177, 1997).

Additionally, vectors expressing the disclosed polynucleotides may be introduced into stem cells taken from the patient and clonally propagated in vitro for autologous transplant back into the same patient.

Routes and frequency of administration, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 3 doses may be administered for a 1–36 week period. Preferably, 3 doses are administered, at intervals of 374 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from Chlamydial infection for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 μg. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897, 268 and 5,075,109.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bortadella pertussis* or *Mycobacterium tuberculosis*. Suitable adjuvants are commercially available as, for example, Freund's Incomplete Adjuvant and Freund's Complete Adjuvant (Difco Laboratories, Detroit, Mich.) and Merck Adjuvant 65 (Merck and Company, Inc., Rahway, N.J.). Other suitable adjuvants include alum, biodegradable microspheres, monophosphoryl lipid A and quil A.

In another aspect, the present invention provides methods for using the polypeptides described above to diagnose Chlamydial infection. In this aspect, methods are provided for detecting Chlamydial infection in a biological sample, using one or more of the above polypeptides, either alone or in combination. For clarity, the term "polypeptide" will be used when describing specific embodiments of the inventive diagnostic methods. However, it will be clear to one of skill in the art that the fusion proteins of the present invention may also be employed in such methods.

As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient. The polypeptides are used in an assay, as described below, to determine the presence or absence of antibodies to the polypeptide(s) in the sample, relative to a predetermined cut-off value. The presence of such antibodies indicates previous sensitization to Chlamydia antigens which may be indicative of Chlamydia-infection.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with Chlamydia. After determining which samples test positive (as described below) with each polypeptide, combinations of two or more polypeptides may be formulated that are capable of detecting infection in most, or all, of the samples tested.

A variety of assay formats are known to those of ordinary skill in the art for using one or more polypeptides to detect antibodies in a sample. See, e.g., Harlow and Lane, *Antibodies: A Laboratoiy Manual*, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate, or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin (BSA) or Tween 20™ (Sigma Chemical Co., St. Louis, Mo.) may be employed. The immobilized polypeptide is then incubated with the sample, and antibody is allowed to bind to the antigen. The sample may be diluted with a suitable dilutent, such as phosphate-buffered saline (PBS) prior to incubation. In general, an appropriate contact time (i.e., incubation time) is that period of time that is sufficient to detect the presence of antibody within an HGE-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-Chlamydia antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for Chlamydia-infection. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, pp. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for Chlamydial infection.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-Chlamydia antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 $\mu$g, and more preferably from about 50 ng to about 500 ng. Such tests can typically be performed with a very small amount (e.g., one drop) of patient serum or blood.

Of course, numerous other assay protocols exist that are suitable for use with the polypeptides of the present invention. The above descriptions are intended to be exemplary only. One example of an alternative assay protocol which may be usefully employed in such methods is a Western blot, wherein the proteins present in a biological sample are separated on a gel, prior to exposure to a binding agent. Such techniques are well known to those of skill in the art.

In yet another aspect, the present invention provides antibodies to the polypeptides of the present invention. Antibodies may be prepared by any of a variety of techniques known to those of ordinary skill in the art. See, e.g., Harlow and Lane, *Antibodies: A Laboratory Manual*, Cold Spring Harbor Laboratory, Cold Spring Harbor, N.Y., 1988. In one such technique, an immunogen comprising the antigenic polypeptide is initially injected into any of a wide variety of mammals (e.g., mice, rats, rabbits, sheep and goats). The polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide or antigenic epitope may then be purified from such antisera by, for example, affinity chromatography using the polypeptide coupled to a suitable solid support.

Monoclonal antibodies specific for the antigenic polypeptide or epitope of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide or antigenic epitope of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses, HAT (hypoxanthine, aminopterin, thymidine) selection. After a sufficient time, usually about 1 to 2 weeks, colonies of hybrids are observed. Single colonies are selected and tested for binding activity against the polypeptide or antigenic epitope. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides or antigenic epitopes of this invention may be used in the purification process in, for example, an affinity chromatography step.

Antibodies may be used in diagnostic tests to detect the presence of Chlamydia antigens using assays similar to those detailed above and other techniques well known to those of skill in the art, thereby providing a method for detecting Chlamydial infection in a patient.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify Chlamydia-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule encoding one of the polypeptides disclosed herein. Preferably, oligonucleotide probes for use in the inventive diagnostic methods comprise at least about 15 contiguous oligonucleotides of a DNA molecule encoding one of the polypeptides disclosed herein. Techniques for both PCR based assays and hybridization assays are well known in the art (see, for example, Mullis et al. Ibid; Ehrlich, Ibid). Primers or probes may thus be used to detect Chlamydia-specific sequences in biological samples. DNA probes or primers comprising oligonucleotide sequences described above may be used alone or in combination with each other.

The following Examples are offered by way of illustration and not by way of limitation.

EXAMPLE 1

Isolation of DNA Sequences Encoding Chlamydia Antigens

Chlamydia antigens of the present invention were isolated by expression cloning of a genomic DNA library of *Chlamydia trachomatis* LGV II essentially as described by Sanderson et al. (*J. Exp. Med.*, 1995, 182:1751–1757) and were shown to induce PBMC proliferation and IFN-γ in an immunoreactive T cell line.

A Chlamydia-specific T cell line was generated by stimulating PBMCs from a normal donor with no history of chlamydial genital tract infection with elementary bodies of *Chlamydia trachomatis* LGV II. This T cell line, referred to as TCL-8, was found to recognize both *Chlamydia trachomatis* and *Chlamydia pneumonia* infected monocyte-derived dendritic cells.

A randomly sheared genomic library of *Chlamydia trachomatis* LGV II was-constructed in Lambda ZAP (Stratagene, La Jolla, Calif.) and the amplified library plated out in 96 well microtiter plates at a density of 30 clones/well. Bacteria were induced to express recombinant protein in the presence of 2 mM IPTG for 3 h, then pelleted and resuspended in 200 µl of RPMI 10% FBS. 10 µl of the induced bacterial suspension was transferred to 96 well plates containing autologous monocyte-derived dendritic cells. After a 2 h incubation, dendritic cells were washed to remove free *E. coli* and Chlamydia-specific T cells were added. Positive *E. coli* pools were identified by determining IFN-γ production and proliferation of the T cells in response to the pools.

Four positive pools were identified, which were broken down to yield four pure clones (referred to as 1-B1-66, 4-D7-28, 3-G3-10 and 10-C10-31), with insert sizes of 481 bp, 183 bp, 110 bp and 1400 bp, respectively. The determined DNA sequences for 1-B1-66, 4-D7-28, 3-G3-10 and 10-C10-31 are provided in SEQ ID NO: 1-4, respectively. Clone 1-B1-66 is approximately in region 536690 of the *C. trachomatis* genome (NCBI *C. trachomatis* database). Within clone 1-B1-66, an open reading frame (ORF) has been identified (nucleotides 115–375) that encodes a previously identified 9 kDa protein (Stephens, et al. Genbank Accession No. AE001320), the sequence of which is provided in SEQ ID NO: 5). Clone 4-D7-28 is a smaller region of the same ORF (amino acids 22–82 of 1-B1-66). Clone 3-G3-10 is approximately in region 74559 of the *C. trachomatis* genome. The insert is cloned in the antisense orientation with respect to its orientation in the genome. The clone 10-C10-31 contains an open reading frame that corresponds to a previously published sequence for S13 ribosomal protein from *Chlamydia trachomatis* (Gu, L. et al. *J Bacteriology*, 177:2594–2601, 1995). The predicted protein sequences for 4-D7-28 and 10-C10-31 are provided in SEQ ID NO: 6 and 12, respectively. Predicted protein sequences for 3-G3-10 are provided in SEQ ID NO: 7–11.

In a related series of screening studies, an additional T cell line was used to screen the genomic DNA library of *Chlamydia trachomatis* LGV II described above. A Chlamlydia-specific T cell line (TCT-1) was derived from a patient with a chlamydial genital tract infection by stimulating patient PBMC with autologous monocyte-derived dendritic cells infected with elementary bodies of *Chlamydia trachomatis* LGV II. One clone, 4C9-18 (SEQ ID NO: 21), containing a 1256 bp insert, elicited a specific immune response, as measured by standard proliferation assays, from the Chlamydia-specific T cell line TCT-1. Subsequent analysis revealed this clone to contain of three known sequences:

lipoamide dehydrogenase (Genbank Accession No. AE001326), disclosed in SEQ ID NO: 22; a hypothetical protein CT429 (Genbank Accession No. AE001316), disclosed in SEQ ID NO: 23; and part of an open reading frame of ubiquinone methyltransferase CT428 (Genbank Accession No. AE001316), disclosed in SEQ ID NO: 24.

To further characterize the open reading frame containing the T cell stimulating epitope(s), a cDNA fragment containing nucleotides 1–695 of clone 4C9-18 with a cDNA sequence encoding a 6x-Histidine tag on the amino terminus was subcloned into the NdeI/EcoRI site of the pET17b vector (Novagen, Madison, Wis.), referred to as clone 4C9-18#2 BL21 pLysS (SEQ ID NO: 25, with the corresponding amino acid sequence provided in SEQ ID NO: 26) and transformed into *E. coli*. Selective induction of the transformed *E. coli* with 2 mM IPTG for three hours resulted in the expression of a 26 kDa protein from clone 4C9-18#2 BL21 pLysS, as evidenced by standard Coomassie-stained SDS-PAGE. To determine the immunogenicity of the protein encoded by clone 4C9-18#2 BL21 pLysS, *E. coli* expressing the 26 kDa protein were titered onto $1 \times 10^4$ monocyte-derived dendritic cells and incubated for two hours. The dendritic cell cultures were washed and $2.5 \times 10^4$ T cells (TCT-1) added and allowed to incubate for an additional 72 hours, at which time the level of IFN-γ in the culture supernatant was determined by ELISA. As shown in FIG. 1, the T-cell line TCT-1 was found to respond to induced cultures as measured by IFN-g, indicating a Chlamydia-specific T-cell response against the lipoamide dehydrogenase sequence. Similarly, the protein encoded by clone 4C9-18#2 BL21 pLysS was shown to stimulate the TCT-1 T-cell line by standard proliferation assays.

EXAMPLE 2

Induction of T Cell Proliferation and Interferon-γ Production by Chlamydia Antigens The ability of recombinant Chlamydia antigens to induce T cell proliferation and interferon-γ production is determined as follows.

Proteins are induced by IPTG and purified by Ni-NTA agarose affinity chromatograph (Webb et al., *J. Immunology* 157:5034–5041, 1996). The purified polypeptides are then screened for the ability to induce T-cell proliferation in PBMC preparations. PBMCs from *C. trachomatis* patients as well as from normal donors whose T-cells are known to proliferate in response to Chlamydia antigens, are cultured in medium comprising RPMI 1640 supplemented with 10% pooled human serum and 50 μg/ml gentamicin. Purified polypeptides are added in duplicate at concentrations of 0.5 to 10 μg/mL. After six days of culture in 96-well round-bottom plates in a volume of 200 μl, 50 μl of medium is removed from each well for determination of IFN-γ levels, as described below. The plates are then pulsed with 1 μCi/well of tritiated thymidine for a further 18 hours, harvested and tritium uptake determined using a gas scintillation counter. Fractions that result in proliferation in both replicates three fold greater than the proliferation observed in cells cultured in medium alone are considered positive.

IFN-γ is measured using an enzyme-linked immunosorbent assay (ELISA). ELISA plates are coated with a mouse monoclonal antibody directed to human IFN-γ (PharMingen, San Diego, Calif.) in PBS for four hours at room temperature. Wells are then blocked with PBS containing 5% (W/V) non-fat dried milk for 1 hour at room temperature. The plates are washed six times in PBS/0.2% TWEEN-20 and samples diluted 1:2 in culture medium in the ELISA plates are incubated overnight at room temperature. The plates are again washed and a polyclonal rabbit anti-human IFN-γ serum diluted 1:3000 in PBS/10% normal goat serum is added to each well. The plates are then incubated for two hours at room temperature, washed and horseradish peroxidase-coupled anti-rabbit IgG (Sigma Chemical So., St. Louis. Mo.) is added at a 1:2000 dilution in PBS/5% non-fat dried milk. After a further two hour incubation at room temperature, the plates are washed and TMB substrate added. The reaction is stopped after 20 min with 1 N sulfuric acid. Optical density is determined at 450 nm using 570 nm as a reference wavelength. Fractions that result in both replicates giving an OD two fold greater than the mean OD from cells cultured in medium alone, plus 3 standard deviations, are considered positive.

Using the above methodology, recombinant 1B1-66 protein (SEQ ID NO: 5) as well as two synthetic peptides corresponding to amino acid residues 49–67 (SEQ ID NO: 13; referred to as 1-B1-66/49-67) and 58-77 (SEQ ID NO: 14, referred to as 1B1-66/58-77), respectively, of SEQ ID NO: 5, were found to induce a proliferative response and IFN-γ production in a Chlamydia-specific T cell line used to screen a genomic library of *C. trachomatis* LGV II. This T cell line recognizes *C. trachomatis* as well as *C. pneumoniae* infected monocyte-derived dendritic cells. These results indicate that the protein 1-B1-66 includes T cell stimulating epitopes, such as 1-B1-66/49-67 and 1B1-66/58-77, which are expressed in both *C. pneumoniae* and *C. trachomatis*.

EXAMPLE 3

Preparation of Synthetic Polypeptides

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugating or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

EXAMPLE 4

Figure 2:
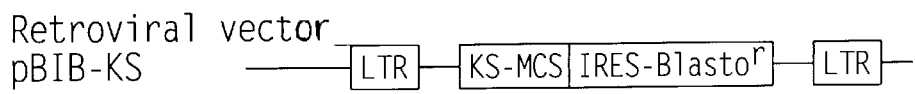
FIG. 2 illustrates retroviral vectors pBIB-KS1,2,3 modified to contain a Kosak translation initiation site and stop codons.

Lysis of Target Cells by a Murine CD8+ T-Cell Line Specific for Chlamydia Antigen A genomic library of *Chlamydia trachomatis* LGV II was constructed by limited digests using BamHI, BglII, BstYi and MboI restriction enzymes. The. restriction digest fragments were subsequently ligated into the BamHI site of the retroviral vectors pBIB-KS1,2,3. This vector set was modified to contain a Kosak translation initiation site and stop codons in order to allow expression of proteins from short DNA genomic fragments, as shown in FIG. 2. DNA pools of 80 clones were prepared and transfected into the retroviral packaging line Phoenix-Ampho, as described in Pear, W. S., Scott, M. L. and Nolan, G. P., Generation of High Titre, Helper-free Retroviruses by Transient Transfection. Methods in Molecular Medicine: Gene Therapy Protocols, Humana Press, Totowa, N.J., pp. 41–57. The Chlamydia library in retroviral form was then transduced into H2-Ld expressing P815 cells, which were then used as target cells to stimulate an antigen specific T-cell line.

A Chlamydia-specific, murine H2-Ld restricted CD8+ T-cell line was expanded in culture by repeated rounds of stimulation with irradiated C. trachomatis-infected J774 cells and irradiated syngeneic spleen cells, as described by Starnbach, M., in J. Immunol., 153:5183, 1994. This Chlamydia-specific T-cell line was used to screen the above Chlamydia genomic library expressed by the retrovirally-transduced P815 cells. Positive DNA pools were identified by detection of IFN-γ production usnig Elispot analysis (SEE Lalvani et al., J. Experimental Medicine 186:859–865, 1997).

Two positive pools, referred to as 2C7 and 2E10, were identified by standard chromium release assays. Stable transductants of P815 cells from pool 2C7 were cloned by limiting dilution and individual clones were selected based upon their capacity to elicit IFN-γ production from the Chlamydia-specific CTL line. From this screening process, four positive clones were selected, referred to as 2C7-8, 2C7-9, 2C7-19 and 2C7-21.

Transgenic DNA from these four positive clones was PCR amplified using pBIB-KS specific primers to selectively amplify the Chlamydia DNA insert. Amplified inserts were gel purified and sequenced. One immunoreactive clone, 2C7-8 (SEQ ID NO: 15, with the predicted amino acid sequence provided in SEQ ID NO: 32), is a 160 bp fragment with homology to nucleotides 597304–597145 of Chlamydia trachomatis, serovar D (NCBI, BLASTN search; SEQ ID NO: 33, with the predicted amino acid sequence provided in SEQ ID NO: 34). The sequence of clone 2C7-8 maps within two putative open reading frames from the region of high homology described immediately above, and in particular, one of these putative open reading frames, consisting of a 298 amino acid fragment (SEQ ID NO: 16, with the predicted amino acid sequence provided in SEQ ID NO: 17), was demonstrated to exhibit immunological activity.

Figure 3:
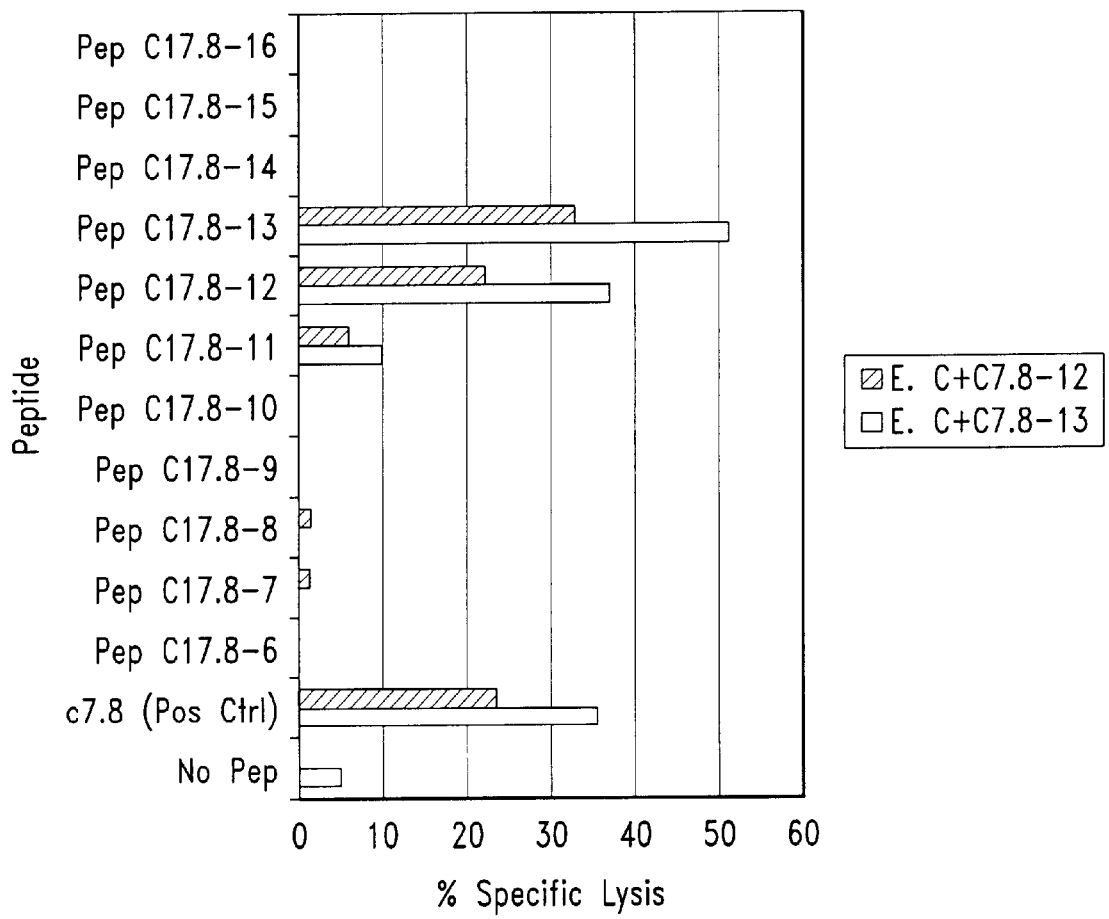
FIG. 3 shows specific lysis in a chromium release assay of P815 cells pulsed with Chlamydia peptides CtC7.8-12 (SEQ ID NO: 18) and CtC7.8-13 (SEQ ID NO: 19).

To determine if these two putative open reading frames (SEQ ID NO: 16 and 20) encoded a protein with an associated immunological function, overlapping peptides (17–20 amino acid lengths) spanning the lengths of the two open reading frames were synthesized, as described in Example 3. A standard chromium release assay was utilized to determine the per cent specific lysis of peptide-pulsed H2-Ld restricted target cells. In this assay, aliquots of P815 cells (H2-Ld) were labeled at 37° C. for one hour with 100 μCi of $^{51}$Cr in the presence or absence of 1 μg/ml of the indicated peptides. Following this incubation, labeled P815 cells were washed to remove excess $^{51}$Cr and peptide, and subsequently plated in duplicate in microculture plates at a concentration of 1,000 cells/well. Effector CTL (Chlamydia-specific CD8 T cells) were added at the indicated effector-:target ratios. Following a 4 hour incubation, supernatants were harvested and measured by gamma-counter for release of $^{51}$Cr into the supernatant. Two overlapping peptides from the 298 amino acid open reading frame did specifically stimulate the CTL line. As shown in FIG. 3, peptides CtC7.8-12 (SEQ ID NO: 18) and CtC7.8-13 (SEQ ID NO: 19) were able to elicit 38 to 52% specific lysis, respectively, at an effector to target ratio of 10:1. Notably, the overlap between these two peptides contained a predicted Ld binding peptide. A 10 amino acid peptide was synthesized to correspond to this overlapping sequence (SEQ ID NO: 31) and was found to generate a strong immune response from the anti-Chlamydia CTL line by elispot assay. Significantly, a search of the most recent Genbank database revealed no proteins have previously been described for this gene.

Therefore, the putative open reading frame encoding clone 2C7-8 (SEQ ID NO: 15) defines a gene which encompasses an antigen from Chlamydia capable of stimulating antigen-specific CD8+ T-cells in a MHC-I restricted manner, demonstrating this antigen could be used to develop a vaccine against Chlamydia.

EXAMPLE 5

Figure 4:
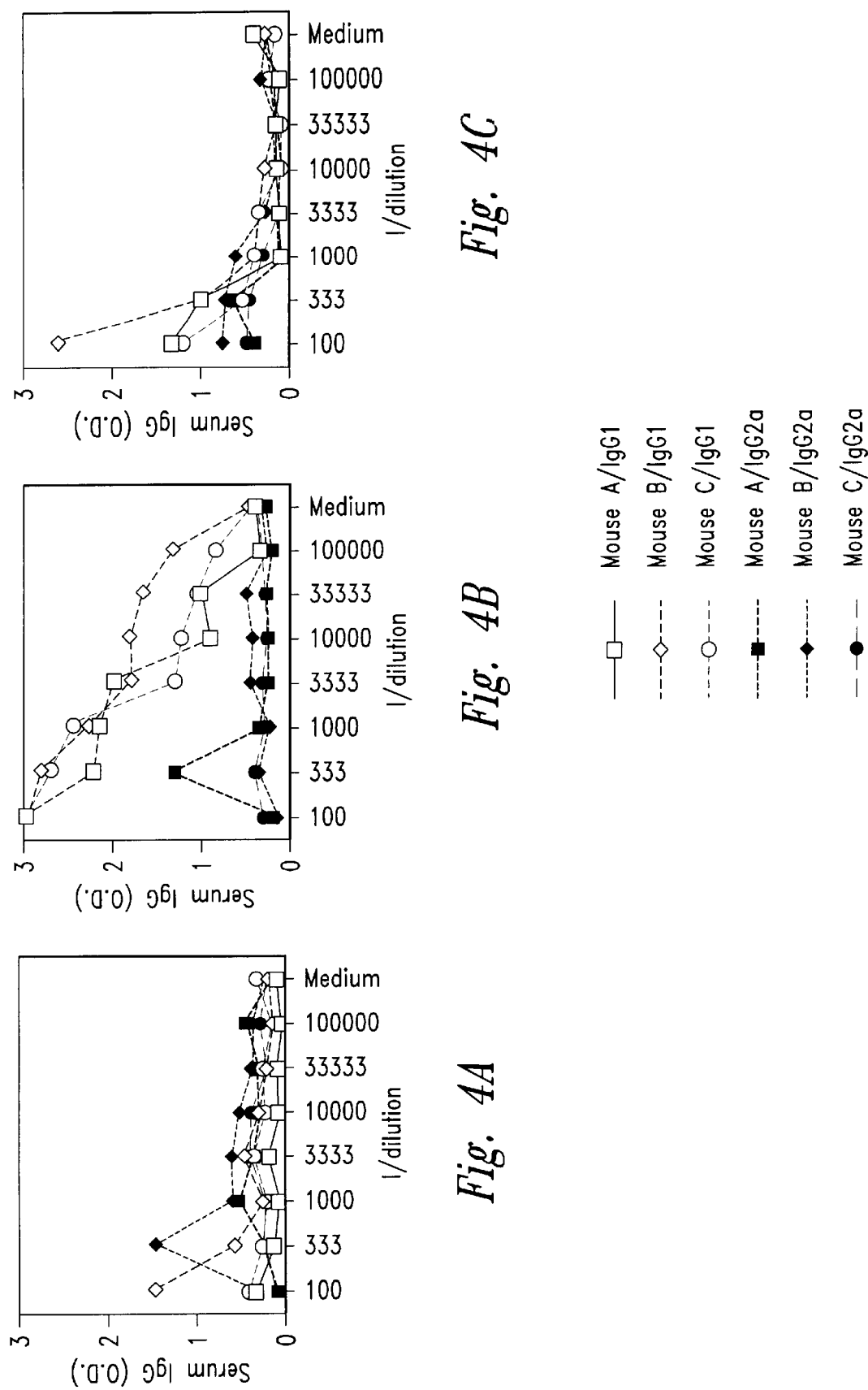
FIG. 4 shows antibody isotype titers in C57B1/6 mice immunized with *C. trachomatis* SWIB protein.

Generation of Antibody and CD4+ T-Cell Responses in Mice Immunized with Chlamydia Antigens Immunogenicity studies were conducted to determine the antibody and CD4+ T cell responses in mice immunized with either purified SWIB or S13 proteins formulated with Montanide adjuvant, or DNA-based immunizations with pcDNA-3 expression vectors containing the DNA sequences for SWIB or S13. SWIB is also referred to as clone 1-B1-66 (SEQ ID NO: 1, with the corresponding amino acid sequence provided in SEQ ID NO: 5), and S13 ribosomal protein is also referred to as clone 10-C10-31 (SEQ ID NO: 4, with the corresponding amino acid sequence provided in SEQ ID NO: 12). In the first experiment, groups of three C57BL/6 mice were immunized twice and monitored for antibody and CD4+ T-cell responses. DNA immunizations were intradermal at the base of the tail and polypeptide immunizations were administered by subcutaneous route. Results from standard $^3$H-incorporation assays of spleen cells from immunized mice shows a strong proliferative response from the group immunized with purified recombinant SWIB polypeptide (SEQ ID NO: 5). Further analysis by cytokine induction assays, as previously described, demonstrated that the group immunized with SWIB polypeptide produced a measurable IFN-γ and IL-4 response. Subsequent ELISA-based assays to determine the predominant antibody isotype response in the experimental group immunized with the SWIB polypeptide were performed. FIG. 4 illustrates the SWIB-immunized group gave a humoral response that was predominantly IgG1.

Figure 5:
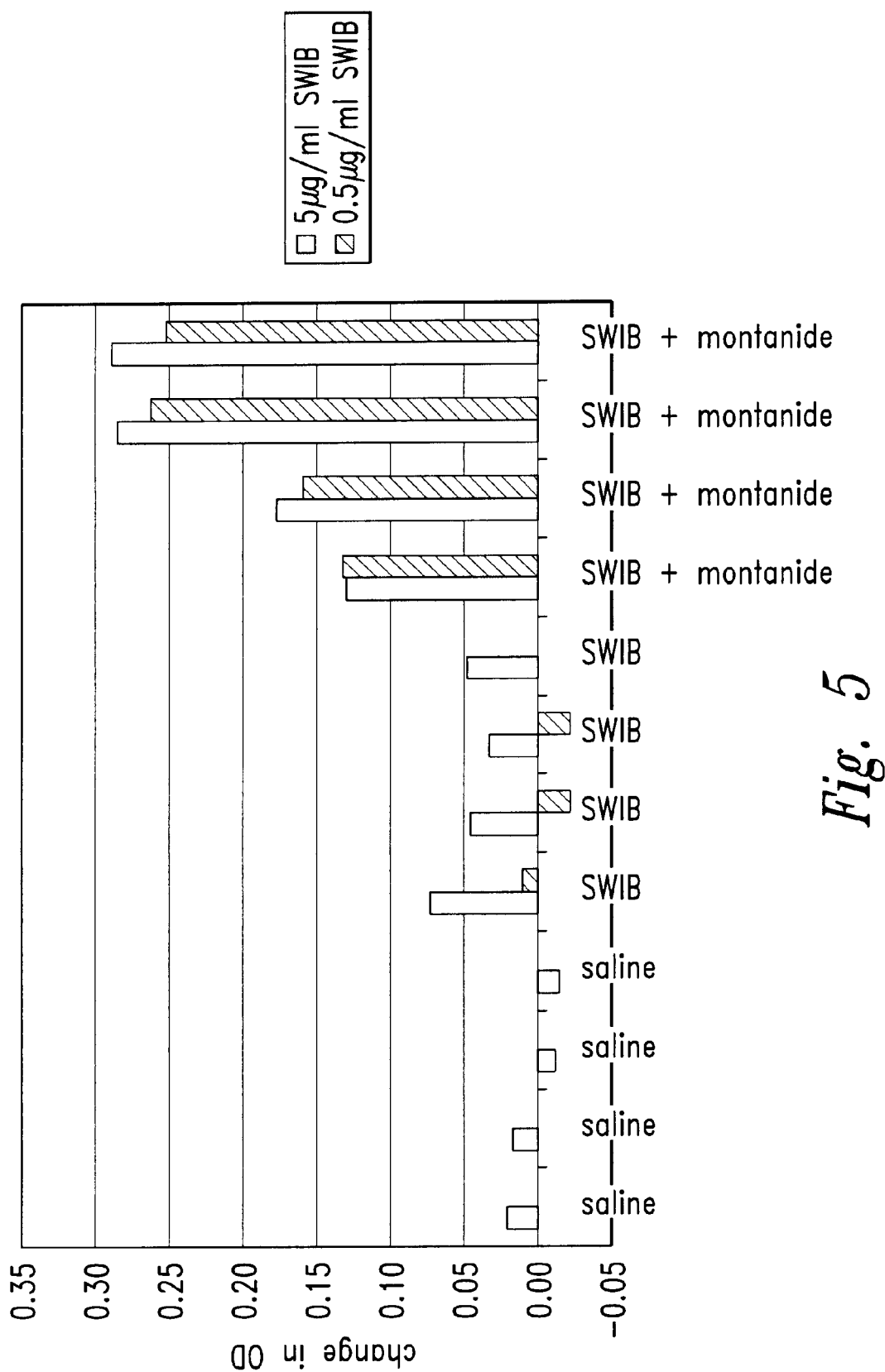
FIG. 5 shows Chlamydia-specific T-cell proliferative responses in splenocytes from C3H mice immunized with *C. trachomatis* SWIB protein.

In a second experiment, C3H mice were. immunized three times with 10 μg purified SWIB protein (also referred to as clone 1-B1-66, SEQ ID NO: 5) formulated in either PBS or Montanide at three week intervals and harvested two weeks after the third immunization. Antibody titers directed against the SWIB protein were determined by standard ELISA-based techniques well known in the art, demonstrating the SWIB protein formulated with Montanide adjuvant induced a strong humoral immune response. T-cell proliferative-responses were determined by a XTT-based assay (Scudiero, et al, Cancer Research, 1988, 48:4827). As shown in FIG. 5, splenocytes from mice immunized with the SWIB polypeptide plus Montanide elicited an antigen specific proliferative response. In addition, the capacity of splenocytes from immunized animals to secrete IFN-γ in response to soluble recombinant SWIB polypeptide was determined using the cytokine induction assay previously described. The splenocytes from all animals in the group immunized with SWIB polypeptide formulated with montanide adjuvant secreted IFN-γ in response to exposure to the SWIB Chlamydia antigen, demonstrating an Chlamydia-specific immune response.

EXAMPLE 6

Expression and Characterization of Chlamydia Pneumoniae Genes

The human T-cell line, TCL-8, described in Example 1, recognizes Chlamydia trachomatis as well as Chlamydia pneumonia infected monocyte-derived dendritic cells, suggesting Chlamydia trachomatis and pneumonia may encode cross-reactive T-cell epitopes. To isolate the Chlamydia pneumonia genes homologous to Chlamydia trachomatis LGV II clones 1B1-66, also referred to as SWIB (SEQ ID NO: 1) and clone 10C10-31, also referred to as S13 ribosomal protein (SEQ ID NO: 4), HeLa 229 cells were infected with C. pneumonia strain TWAR (CDC/CWL-029). After three days incubation, the C. pneumonia-infected HeLa cells were harvested, washed and resuspended in 200 μl water and heated in a boiling water bath for 20 minutes. Ten microliters of the disrupted cell suspension was used as the PCR template.

Figure 7A:
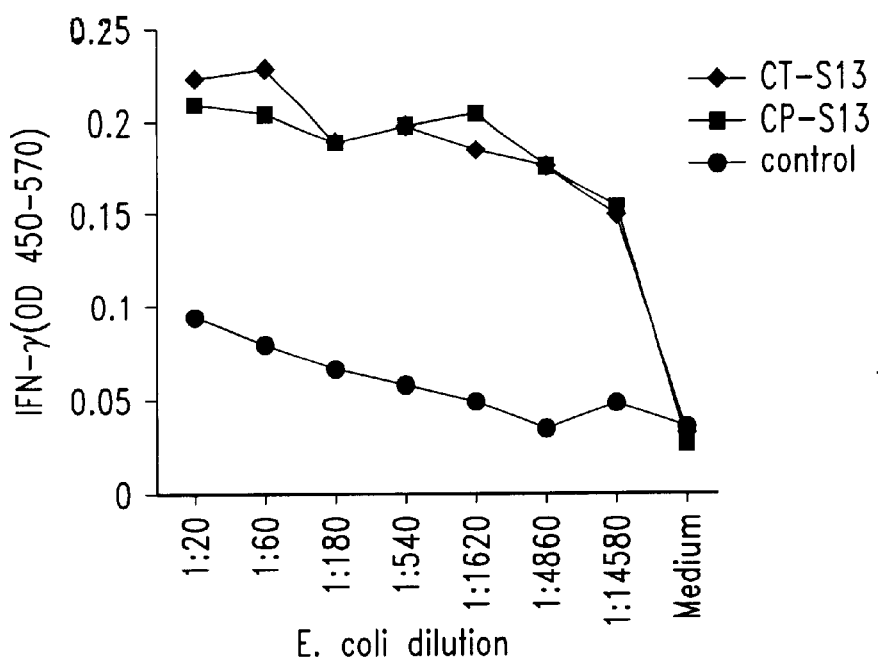
FIGS. 7A and 7B show induction of IFN-γ from a human anti-chlamydia T-cell line (TCL-8) capable of cross-reacting to *C. trachomatis* and *C. pneumonia* upon activation by monocyte-derived dendritic cells expressing chlamydial proteins
Figure 7B:
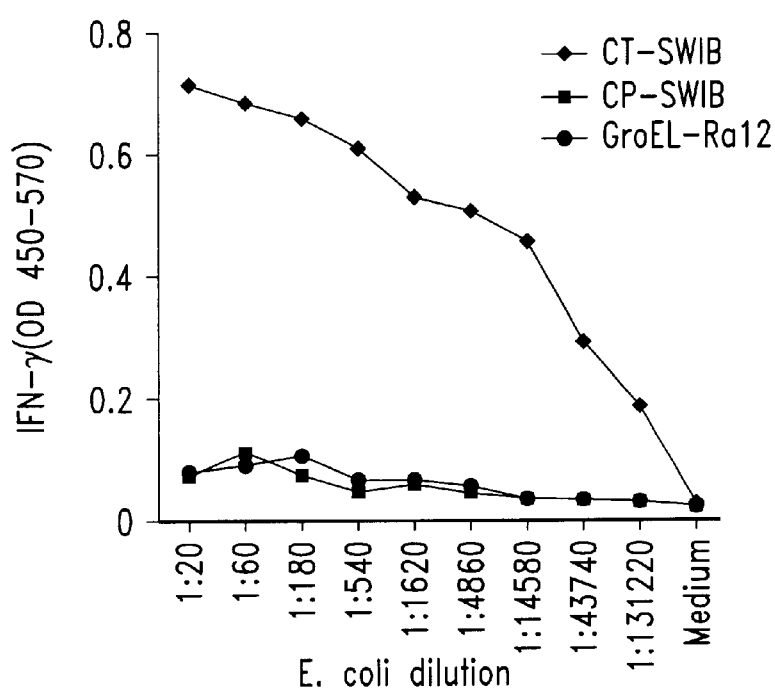

C. pneumonia specific primers were designed for clones 1B1-66 and 10C10-31 such that the 5' end had a 6X-Histidine tag and a Nde I site inserted, and the 3" end had a stop codon and a BamHI site included (FIG. 6). The PCR products were amplified and sequenced by standard techniques well known in the art. The C. pneumonia-specific PCR products were cloned into expression vector pET17B (Novagen, Madison, Wis.) and transfected into E. coli BL21 pLysS for expression and subsequent purification utilizing the histidine-nickel chromatographic methodology provided by Novagen. Two proteins from C. pneumonia were thus generated, a 10 kDa protein referred to as CpSWIB (SEQ ID NO: 27 with the corresponding amino acid sequence provided in SEQ ID NO: 28), a 15 kDa protein referred to as CpS13 (SEQ ID NO: 29 with the corresponding amino acid sequence provided in SEQ ID NO: 30). A human anti-chlamydia T-cell line (TCL-8) capable of cross-reacting to C. trachomatis and C. pneumonia was used to determine whether the expressed proteins possessed T-cell epitopes common to both C. trachomatis and C. pneumonia. Briefly, E. coli expressing chlamydial proteins were titered on $1 \times 10^4$ monocyte-derived dendritic cells. After two hours, the dendritic cells cultures were washed and $2.5 \times 10^4$ T cells (TCL-8) added and allowed to incubate for an additional 72 hours. The amount of INF-γ in the culture supernatant was then determined by ELISA. As shown in FIGS. 7A and 7B, the TCL-8 T-cell line specifically recognized the S13 ribosomal protein from both C. trachomatis and C. pneumonia as demonstrated by the antigen-specific induction of IFN-γ, whereas only the SWIB protein from C. trachomatis was recognized by the T-cell line. To validate these results, the T cell epitope of C. trachomatis SWIB was identified by epitope mapping using target cells pulsed with a series of overlapping peptides and the T-cell line TCL-8. 3H-thymidine incorporation assays demonstrated that the peptide, referred to as C.t.SWIB 52-67, of SEQ ID NO: 39 gave the strongest proliferation of the TCL-8 line. The homologous peptides corresponding to the SWIB of C. pnuemoniae sequence (SEQ ID NO: 40), the topoisomerase-SWIB fusion of C. pnuemoniae (SEQ ID NO: 43) and C. trachomatis (SEQ ID NO: 42) as well as the human SWI domain (SEQ ID NO: 41) were synthesized and tested in the above assay. The T-cell line TCL-8 only recognized the C. trachomatis peptide of SEQ ID NO: 39 and not the corresponding C. pnuemoniae peptide (SEQ ID NO: 40), or the other corresponding peptides described above (SEQ ID NO; 41–43).

Although the present invention has been described in some detail by way of illustration and example for purposes of clarity of understanding, changes and modifications can be carried out without departing from the scope of the invention which is intended to be limited only by the scope of the appended claims.

What is claimed is:

1. An isolated polypeptide comprising the amino acid sequence of SEQ ID NO:26, 28, 30 or 32, encoded by the polynucleotide sequences of SEQ ID NO:21, 27, 29, and 15, respectively.

2. A fusion protein comprising the polypeptide of claim 1.

3. A composition comprising the polypeptide of claim 1, and a physiologically acceptable carrier.

4. A composition comprising an isolated polypeptide of claim 1 and a physiologically acceptable carrier.

5. A composition comprising an isolated polypeptide and a physiologically acceptable carrier, wherein the polypeptide comprises the amino acid sequence of SEQ ID NO:28.

6. A diagnostic kit comprising:
(a) an isolated polypeptide comprising a Chlamydia antigen, wherein said antigen comprises the amino acid sequence of SEQ ID NO:26, 28, 30 or 32, encoded by the polynucleotide sequences of SEQ ID NO:21, 27, 29, and 15, respectively and
(b) a detection reagent.

7. A diagnostic kit comprising:
(a) a fusion protein comprising a polypeptide, the polypeptide comprising a Chlamydia antigen, wherein said antigen comprises the amino acid sequence of SEQ ID NO:26, 28, 30 or 32, encoded by the polynucleotide sequences of SEQ ID NO:21, 27, 29, and 15, respectively; and
(b) a detection reagent.

8. The kit of claims 6 or 7 wherein the polypeptide is immobilized on a solid support.

9. The kit of claims 6 or 7 wherein the detection reagent comprises a reporter group conjugated to a binding agent.

10. The kit of claim 9 wherein the binding agent is selected from the group consisting of anti-immunoglobulins, Protein G, Protein A and lectins.

11. The kit of claim 9 wherein the reporter group is selected from the group consisting of radioisotopes, fluorescent groups, luminescent groups, enzymes, biotin and dye particles.

12. An isolated polypeptide comprising an immunogenic epitope comprising the amino acid sequence of SEQ ID NO: 18.

13. An isolated polypeptide comprising an immunogenic epitope comprising the amino acid sequence of SEQ ID NO: 19.

14. An isolated polypeptide comprising an immunogenic portion of a Chlamydia antigen, wherein said portion comprises the amino acid sequence selected from the group consisting of SEQ ID NO: 18, 19, 31 and 39.

* * * * *

UNITED STATES PATENT AND TRADEMARK OFFICE
CERTIFICATE OF CORRECTION

PATENT NO. : 6,447,779 B1
DATED : September 10, 2002
INVENTOR(S) : Peter Probst et al.

It is certified that error appears in the above-identified patent and that said Letters Patent is hereby corrected as shown below:

<u>Title page,</u>
Item [56], References Cited, FOREIGN PATENT DOCUMENTS, should include the following reference:
-- WO          WO 01/40474          06/07/01 --.
OTHER PUBLICATIONS,
"Indentification of a CD4$^+$ T Cell-stimulating Antigen of Pathogenic Bacteria by Expression Cloning," *J. Exp. Med.* 182(6):1751-1757, 1995." should read
-- Sanderson et al., "Identification of a CD4$^+$ T Cell-stimulating Antigen of Pathogenic Bacteria by Expression Cloning," *J. Exp. Med.* 182(6):1751-1757, 1995. --.

Signed and Sealed this

Eighteenth Day of November, 2003

JAMES E. ROGAN
*Director of the United States Patent and Trademark Office*

SEQUENCE LISTING

<160> NUMBER OF SEQ ID NOS: 49

<210> SEQ ID NO 1
<211> LENGTH: 481
<212> TYPE: DNA
<213> ORGANISM: Chlamydia trachomatis

<400> SEQUENCE: 1

```
ctgaagactt ggctatgttt tttattttga cgataaacct agttaaggca taaaagagtt      60
gcgaaggaag agccctcaac ttttcttatc accttcttta actaggagtc atccatgagt     120
caaaataaga actctgcttt catgcagcct gtgaacgtat ccgctgattt agctgccatc     180
gttggtgcag gacctatgcc tcgcacagag atcattaaga aaatgtggga ttacattaag     240
gagaatagtc ttcaagatcc tacaaacaaa cgtaatatca atcccgatga taaattggct     300
aaagtttttg gaactgaaaa acctatcgat atgttccaaa tgacaaaaat ggtttctcaa     360
cacatcatta ataaaatag aaattgactc acgtgttcct cgtctttaag atgaggaact     420
agttcattct ttttgttcgt ttttgtgggt attactgtat ctttaacaac tatcttagca     480
g                                                                     481
```

<210> SEQ ID NO 2
<211> LENGTH: 183
<212> TYPE: DNA
<213> ORGANISM: Chlamydia trachomatis -continued

```
<400> SEQUENCE: 2
atcgttggtg caggacctat gcctcgcaca gagatcatta agaaaatgtg ggattacatt      60
aaggagaata gtcttcaaga tcctacaaac aaacgtaata tcaatcccga tgataaattg     120
gctaaagttt ttggaactga aaaacctatc gatatgttcc aaatgacaaa atggtttct     180 caa                                                                   183

<210> SEQ ID NO 3
<211> LENGTH: 110
<212> TYPE: DNA
<213> ORGANISM: Chlamydia trachomatis

<400> SEQUENCE: 3
gctgcgacat catgcgagct tgcaaaccaa catggacatc tccaatttcc ccttctaact      60
cgctctttgg aactaatgct gctaccgagt caatcacaat cacatcgacc                110

<210> SEQ ID NO 4
<211> LENGTH: 555
<212> TYPE: DNA
<213> ORGANISM: Chlamydia trachomatis

<400> SEQUENCE: 4
cggcacgagc ctaagatgct tatactactt taagggaggc ccttcgtatg ccgcgcatca      60
ttggaataga tattcctgcg aaaagaaat taaaaataag tcttacatat atttatggaa     120
tagggccagc tctttctaaa gagattattg ctagattgca gttgaatccc gaagctagag     180
ctgcagagtt gactgaggaa gaggttggtc gactaaacgc tctttttacag tcggattacg     240 ttgttgaagg ggatttgcgc cgtcgtgtgc aatctgatat caaacgtctg attactatcc     300
atgcttatcg tggacaaaga catagacttt ctttgcctgt tcgtggtcag agaacaaaaa     360
caaattctcg cacgcgtaag ggtaaacgta aaactattgc aggtaagaag aaataataat     420
ttttaggaga gagtgttttg gttaaaaatc aagcgcaaaa aagaggcgta aaaagaaaac     480
aagtaaaaaa cattccttcg ggcgttgtcc atgttaaggc tacttttaat aatacaattg     540
taaccataac agacc                                                      555

<210> SEQ ID NO 5
<211> LENGTH: 86
<212> TYPE: PRT
<213> ORGANISM: Chlamydia trachomatis

<400> SEQUENCE: 5

Met Ser Gln Asn Lys Asn Ser Ala Phe Met Gln Pro Val Asn Val Ser
 1               5                  10                  15

Ala Asp Leu Ala Ala Ile Val Gly Ala Gly Pro Met Pro Arg Thr Glu
                20                  25                  30

Ile Ile Lys Lys Met Trp Asp Tyr Ile Lys Glu Asn Ser Leu Gln Asp
            35                  40                  45

Pro Thr Asn Lys Arg Asn Ile Asn Pro Asp Asp Lys Leu Ala Lys Val
        50                  55                  60

Phe Gly Thr Glu Lys Pro Ile Asp Met Phe Gln Met Thr Lys Met Val
65                  70                  75                  80

Ser Gln His Ile Ile Lys
                85

<210> SEQ ID NO 6
<211> LENGTH: 61
```

-continued

<212> TYPE: PRT
<213> ORGANISM: Chlamydia trachomatis

<400> SEQUENCE: 6

```
Ile Val Gly Ala Gly Pro Met Pro Arg Thr Glu Ile Ile Lys Lys Met
 1               5                  10                  15

Trp Asp Tyr Ile Lys Glu Asn Ser Leu Gln Asp Pro Thr Asn Lys Arg
            20                  25                  30

Asn Ile Asn Pro Asp Asp Lys Leu Ala Lys Val Phe Gly Thr Glu Lys
        35                  40                  45

Pro Ile Asp Met Phe Gln Met Thr Lys Met Val Ser Gln
    50                  55                  60
```

<210> SEQ ID NO 7
<211> LENGTH: 36
<212> TYPE: PRT
<213> ORGANISM: Chlamyida trachomatis

<400> SEQUENCE: 7

```
Ala Ala Thr Ser Cys Glu Leu Ala Asn Gln His Gly His Leu Gln Phe
 1               5                  10                  15

Pro Leu Leu Thr Arg Ser Leu Glu Leu Met Leu Leu Pro Ser Gln Ser
            20                  25                  30

Gln Ser His Arg
        35
```

<210> SEQ ID NO 8
<211> LENGTH: 18
<212> TYPE: PRT
<213> ORGANISM: Chlamydia trachomatis

<400> SEQUENCE: 8

```
Leu Arg His His Ala Ser Leu Gln Thr Asn Met Asp Ile Ser Asn Phe
 1               5                  10                  15

Pro Phe
```

<210> SEQ ID NO 9
<211> LENGTH: 5
<212> TYPE: PRT
<213> ORGANISM: Chlamydia trachomatis

<400> SEQUENCE: 9

```
Leu Ala Leu Trp Asn
 1               5
```

<210> SEQ ID NO 10
<211> LENGTH: 11
<212> TYPE: PRT
<213> ORGANISM: Chlamydia trachomatis

<400> SEQUENCE: 10

```
Cys Cys Tyr Arg Val Asn His Asn His Ile Asp
 1               5                  10
```

<210> SEQ ID NO 11
<211> LENGTH: 36
<212> TYPE: PRT
<213> ORGANISM: Chlamydia trachomatis

<400> SEQUENCE: 11

```
Val Asp Val Ile Val Ile Asp Ser Val Ala Ala Leu Val Pro Lys Ser
 1               5                  10                  15
```

Glu Leu Glu Gly Glu Ile Gly Asp Val His Val Gly Leu Gln Ala Arg
            20                  25                  30

Met Met Ser Gln
        35

<210> SEQ ID NO 12
<211> LENGTH: 122
<212> TYPE: PRT
<213> ORGANISM: Chlamydia trachomatis

<400> SEQUENCE: 12

Met Pro Arg Ile Ile Gly Ile Asp Ile Pro Ala Lys Lys Leu Lys
 1               5                  10                  15

Ile Ser Leu Thr Tyr Ile Tyr Gly Ile Gly Pro Ala Leu Ser Lys Glu
            20                  25                  30

Ile Ile Ala Arg Leu Gln Leu Asn Pro Glu Ala Arg Ala Ala Glu Leu
        35                  40                  45

Thr Glu Glu Val Gly Arg Leu Asn Ala Leu Leu Gln Ser Asp Tyr
    50                  55                  60

Val Val Glu Gly Asp Leu Arg Arg Val Gln Ser Asp Ile Lys Arg
65                  70                  75                  80

Leu Ile Thr Ile His Ala Tyr Arg Gly Gln Arg His Arg Leu Ser Leu
                85                  90                  95

Pro Val Arg Gly Gln Arg Thr Lys Thr Asn Ser Arg Thr Arg Lys Gly
            100                 105                 110

Lys Arg Lys Thr Ile Ala Gly Lys Lys Lys
        115                 120

<210> SEQ ID NO 13
<211> LENGTH: 20
<212> TYPE: PRT
<213> ORGANISM: Chlamydia trachomatis

<400> SEQUENCE: 13

Asp Pro Thr Asn Lys Arg Asn Ile Asn Pro Asp Lys Leu Ala Lys
 1               5                  10                  15

Val Phe Gly Thr
        20

<210> SEQ ID NO 14
<211> LENGTH: 20
<212> TYPE: PRT
<213> ORGANISM: Chlamydia trachomatis

<400> SEQUENCE: 14

Asp Asp Lys Leu Ala Lys Val Phe Gly Thr Glu Lys Pro Ile Asp Met
 1               5                  10                  15

Phe Gln Met Thr
        20

<210> SEQ ID NO 15
<211> LENGTH: 161
<212> TYPE: DNA
<213> ORGANISM: Chlymidia trachomatis

<400> SEQUENCE: 15
atctttgtgt gtctcataag cgcagagcgg ctgcggctgt ctgtagcttc atcggaggaa      60
ttacctacct cgcgacattc ggagctatcc gtccgattct gtttgtcaac aaaatgctgg    120

```
cgcaaccgtt tctttcttcc caaactaaag caaatatggg a                    161
```

<210> SEQ ID NO 16
<211> LENGTH: 897
<212> TYPE: DNA
<213> ORGANISM: Chlymidia trachomatis

<400> SEQUENCE: 16

```
atggcttcta tatgcggacg tttagggtct ggtacaggga atgctctaaa agcttttttt    60
acacagccca acaataaaat ggcaagggta gtaaataaga cgaagggaat ggataagact   120
attaaggttg ccaagtctgc tgccgaattg accgcaaata ttttggaaca agctggaggc   180
gcgggctctt ccgcacacat tacagcttcc caagtgtcca aaggattagg ggatgcgaga   240
actgttgtcg ctttagggaa tgcctttaac ggagcgttgc caggaacagt tcaaagtgcg   300
caaagcttct tctctcacat gaaagctgct agtcagaaaa cgcaagaagg ggatgagggg   360
ctcacagcag atctttgtgt gtctcataag cgcagagcgg ctgcggctgt ctgtagcatc   420
atcggaggaa ttacctacct cgcgacattc ggagctatcc gtccgattct gtttgtcaac   480
aaaatgctgg caaaaccgtt tctttcttcc caaactaaag caaatatggg atcttctgtt   540
agctatatta tggcggctaa ccatgcagcg tctgtggtgg gtgctggact cgctatcagt   600
gcggaaagag cagattgcga agcccgctgc gctcgtattg cgagagaaga gtcgttactc   660
gaagtgccgg gagaggaaaa tgcttgcgag aagaaagtcg ctggagagaa agccaagacg   720
ttcacgcgca tcaagtatgc actcctcact atgctcgaga agttttggga atgcgttgcc   780
gacgttttca aattggtgcc gctgcctatt acaatgggta ttcgtgcgat tgtggctgct   840
ggatgtacgt tcacttctgc aattattgga ttgtgcactt tctgcgccag agcataa    897
```

<210> SEQ ID NO 17
<211> LENGTH: 298
<212> TYPE: PRT
<213> ORGANISM: Chlamydia trachomatis

<400> SEQUENCE: 17

```
Met Ala Ser Ile Cys Gly Arg Leu Gly Ser Gly Thr Gly Asn Ala Leu
  1               5                  10                  15

Lys Ala Phe Phe Thr Gln Pro Asn Asn Lys Met Ala Arg Val Val Asn
             20                  25                  30

Lys Thr Lys Gly Met Asp Lys Thr Ile Lys Val Ala Lys Ser Ala Ala
         35                  40                  45

Glu Leu Thr Ala Asn Ile Leu Glu Gln Ala Gly Gly Ala Gly Ser Ser
     50                  55                  60

Ala His Ile Thr Ala Ser Gln Val Ser Lys Gly Leu Gly Asp Ala Arg
 65                  70                  75                  80

Thr Val Val Ala Leu Gly Asn Ala Phe Asn Gly Ala Leu Pro Gly Thr
                 85                  90                  95

Val Gln Ser Ala Gln Ser Phe Phe Ser His Met Lys Ala Ala Ser Gln
            100                 105                 110

Lys Thr Gln Glu Gly Asp Glu Gly Leu Thr Ala Asp Leu Cys Val Ser
        115                 120                 125

His Lys Arg Arg Ala Ala Ala Val Cys Ser Ile Ile Gly Gly Ile
    130                 135                 140

Thr Tyr Leu Ala Thr Phe Gly Ala Ile Arg Pro Ile Leu Phe Val Asn
145                 150                 155                 160

Lys Met Leu Ala Lys Pro Phe Leu Ser Ser Gln Thr Lys Ala Asn Met
```

```
                    165                 170                 175
Gly Ser Ser Val Ser Tyr Ile Met Ala Ala Asn His Ala Ala Ser Val
                180                 185                 190
Val Gly Ala Gly Leu Ala Ile Ser Ala Glu Arg Ala Asp Cys Glu Ala
            195                 200                 205
Arg Cys Ala Arg Ile Ala Arg Glu Glu Ser Leu Leu Glu Val Pro Gly
        210                 215                 220
Glu Glu Asn Ala Cys Glu Lys Val Ala Gly Lys Ala Lys Thr
225                 230                 235                 240
Phe Thr Arg Ile Lys Tyr Ala Leu Leu Thr Met Leu Glu Lys Phe Leu
                245                 250                 255
Glu Cys Val Ala Asp Val Phe Lys Leu Val Pro Leu Pro Ile Thr Met
            260                 265                 270
Gly Ile Arg Ala Ile Val Ala Ala Gly Cys Thr Phe Thr Ser Ala Ile
        275                 280                 285
Ile Gly Leu Cys Thr Phe Cys Ala Arg Ala
    290                 295
```

<210> SEQ ID NO 18
<211> LENGTH: 18
<212> TYPE: PRT
<213> ORGANISM: Chlamydia trachomatis

<400> SEQUENCE: 18

```
Arg Ala Ala Ala Ala Ala Val Cys Ser Phe Ile Gly Gly Ile Thr
1               5                   10                  15
Tyr Leu
```

<210> SEQ ID NO 19
<211> LENGTH: 18
<212> TYPE: PRT
<213> ORGANISM: Chlamydia trachomatis

<400> SEQUENCE: 19

```
Cys Ser Phe Ile Gly Gly Ile Thr Tyr Leu Ala Thr Phe Gly Ala Ile
1               5                   10                  15
Arg Pro
```

<210> SEQ ID NO 20
<211> LENGTH: 216
<212> TYPE: PRT
<213> ORGANISM: Chlamydia trachomatis

<400> SEQUENCE: 20

```
Met Arg Gly Ser Gln Gln Ile Phe Val Cys Leu Ile Ser Ala Glu Arg
1               5                   10                  15
Leu Arg Leu Ser Val Ala Ser Ser Glu Glu Leu Pro Thr Ser Arg His
                20                  25                  30
Ser Glu Leu Ser Val Arg Phe Cys Leu Ser Thr Lys Cys Trp Gln Asn
            35                  40                  45
Arg Phe Phe Leu Pro Lys Leu Lys Gln Ile Trp Asp Leu Leu Ala
    50                  55                  60
Ile Leu Trp Arg Leu Thr Met Gln Arg Leu Trp Trp Val Leu Asp Ser
65                  70                  75                  80
Leu Ser Val Arg Lys Glu Gln Ile Ala Lys Pro Ala Leu Val Leu
                85                  90                  95
Arg Glu Lys Ser Arg Tyr Ser Lys Cys Arg Glu Arg Lys Met Leu Ala
```

```
                100              105              110
Arg Arg Lys Ser Leu Glu Arg Lys Pro Arg Arg Ser Arg Ala Ser Ser
        115              120              125

Met His Ser Ser Leu Cys Ser Arg Ser Phe Trp Asn Ala Leu Pro Thr
130              135              140

Phe Ser Asn Trp Cys Arg Cys Leu Leu Gln Trp Val Phe Val Arg Leu
145             150              155              160

Trp Leu Leu Asp Val Arg Ser Leu Leu Gln Leu Leu Asp Cys Ala Leu
                165              170              175

Ser Ala Pro Glu His Lys Gly Phe Phe Lys Phe Leu Lys Lys Lys Ala
            180              185              190

Val Ser Lys Lys Gln Pro Phe Leu Ser Thr Lys Cys Leu Ala Phe
        195              200              205

Leu Ile Val Lys Ile Val Phe Leu
    210              215

<210> SEQ ID NO 21
<211> LENGTH: 1256
<212> TYPE: DNA
<213> ORGANISM: Chlamydia trachomatis

<400> SEQUENCE: 21
ctcgtgccgg cacgagcaaa gaaatccctc aaaaaatggc cattattggc ggtggtgtga      60
tcggttgcga attcgcttcc ttattccata cgttaggctc cgaagtttct gtgatcgaag     120
caagctctca atccttgct tgaataatc cagatatttc aaaaaccatg ttcgataaat       180
tcacccgaca aggactccgt ttcgtactag aagcctctgt atcaaatatt gaggatatag     240
gagatcgcgt tcggttaact atcaatggga atgtcgaaga atacgattac gttctcgtat     300
ctataggacg ccgtttgaat acagaaaata ttggcttgga taaagctggt gttatttgtg    360
atgaacgcgg agtcatccct accgatgcca caatgcgcac aaacgtacct aacatttatg    420
ctattggaga tatcacagga aaatggcaac ttgcccatgt agcttctcat caaggaatca    480
ttgcagcacg gaatataggt ggccataaag aggaaatcga ttactctgct gtcccttctg    540
tgatctttac cttccctgaa gtcgcttcag taggcctctc cccaacagca gctcaacaac    600
atctccttct tcgcttactt tttctgaaaa atttgataca gaagaagaat tcctcgcaca    660
cttgcgagga ggagggcgtc tggaagacca gttgaattta gctaagtttt ctgagcgttt    720
tgattctttg cgagaattat ccgctaagct tggttacgat agcgatggag agactgggga    780
tttcttcaac gaggagtacg acgacgaaga gaggaaatc aaaccgaaga aaactacgaa      840
acgtggacgt aagaagagcc gttcataagc cttgctttta aggtttggta gttttacttc    900
tctaaaatcc aaatggttgc tgtgccaaaa agtagtttgc gtttccggat agggcgtaaa    960
tgcgctgcat gaaagattgc ttcgagagcg gcatcgcgtg ggagatcccg gatactttct   1020
ttcagatacg aataagcata gctgttccca gaataaaaac ggccgacgct aggaacaaca   1080
agatttagat agagcttgtg tagcaggtaa actgggttat atgttgctgg gcgtgttagt   1140
tctagaatac ccaagtgtcc tccaggttgt aatactcgat acacttccct aagagcctct   1200
aatggatagg ataagttccg taatccatag gccatagaag ctaaacgaaa cgtatt        1256

<210> SEQ ID NO 22
<211> LENGTH: 601
<212> TYPE: DNA
<213> ORGANISM: Chlamydia trachomatis
```

<400> SEQUENCE: 22

```
ctcgtgccgg cacgagcaaa gaaatccctc aaaaaatggc cattattggc ggtggtgtga      60
tcggttgcga attcgcttcc ttattccata cgttaggctc cgaagtttct gtgatcgaag     120
caagctctca atccttgctt tgaataatc cagatatttc aaaaaccatg ttcgataaat      180
tcacccgaca aggactccgt ttcgtactag aagcctctgt atcaaatatt gaggatatag     240
gagatcgcgt tcggttaact atcaatggga atgtcgaaga atacgattac gttctcgtat     300
ctataggacg ccgtttgaat acagaaaata ttggcttgga taaagctggt gttatttgtg     360
atgaacgcgg agtcatccct accgatgcca caatgcgcac aaacgtacct aacatttatg     420
ctattggaga tatcacagga aaatggcaac ttgcccatgt agcttctcat caaggaatca     480
ttgcagcacg gaatataggt ggccataaag aggaaatcga ttactctgct gtcccttctg     540
tgatctttac cttccctgaa gtcgcttcag taggcctctc cccaacagca gctcaacaac     600
a                                                                    601
```

<210> SEQ ID NO 23
<211> LENGTH: 270
<212> TYPE: DNA
<213> ORGANISM: Chlamydia trachomatis

<400> SEQUENCE: 23

```
acatctcctt cttcgcttac ttttctgaa aaatttgata cagaagaaga attcctcgca       60
cacttgcgag gaggagggcg tctggaagac cagttgaatt tagctaagtt ttctgagcgt     120
tttgattctt tgcgagaatt atccgctaag cttggttacg atagcgatgg agagactggg     180
gatttcttca cgaggagta cgacgacgaa gaagaggaaa tcaaaccgaa gaaaactacg      240
aaacgtggac gtaagaagag ccgttcataa                                      270
```

<210> SEQ ID NO 24
<211> LENGTH: 363
<212> TYPE: DNA
<213> ORGANISM: Chlamydia trachomatis

<400> SEQUENCE: 24

```
ttacttctct aaaatccaaa tggttgctgt gccaaaaagt agtttgcgtt tccggatagg      60
gcgtaaatgc gctgcatgaa agattgcttc gagagcggca tcgcgtggga gatcccggat     120
actttctttc agatacgaat aagcatagct gttcccagaa taaaaacggc cgacgctagg     180
aacaacaaga tttagataga gcttgtgtag caggtaaact gggttatatg ttgctgggcg     240
tgttagttct agaataccca agtgtcctcc aggttgtaat actcgataca cttccctaag     300
agcctctaat ggataggata agttccgtaa tccataggcc atagaagcta acgaaacgt      360
att                                                                   363
```

<210> SEQ ID NO 25
<211> LENGTH: 696
<212> TYPE: DNA
<213> ORGANISM: Chlamydia trachomatis

<400> SEQUENCE: 25

```
gctcgtgccg gcacgagcaa agaaatccct caaaaaatgg ccattattgg cggtggtgtg      60
atcggttgcg aattcgcttc cttattccat acgttaggct ccgaagtttc tgtgatcgaa     120
gcaagctctc aatccttgct tttgaataat ccagatattt caaaaaccat gttcgataaa     180
ttcacccgac aaggactccg tttcgtacta gaagcctctg tatcaaatat tgaggatata     240
```

-continued

```
ggagatcgcg ttcggttaac tatcaatggg aatgtcgaag aatacgatta cgttctcgta      300
tctataggac gccgtttgaa tacagaaaat attggcttgg ataaagctgg tgttatttgt      360
gatgaacgcg gagtcatccc taccgatgcc acaatgcgca caaacgtacc taacatttat      420
gctattggag atatcacagg aaaatggcaa cttgcccatg tagcttctca tcaaggaatc      480
attgcagcac ggaatatagg tggccataaa gaggaaatcg attactctgc tgtcccttct      540
gtgatcttta ccttccctga agtcgcttca gtaggcctct ccccaacagc agctcaacaa      600
catctccttc tttcgcttact tttttctgaaa aatttgatac agaagaagaa ttcctcgcac      660
acttgcgagg aggagggcgt ctggaagacc agttga                                696
```

<210> SEQ ID NO 26
<211> LENGTH: 231
<212> TYPE: PRT
<213> ORGANISM: Chlamydia trachomatis

<400> SEQUENCE: 26

```
Ala Arg Ala Gly Thr Ser Lys Glu Ile Pro Gln Lys Met Ala Ile Ile
  1               5                  10                  15

Gly Gly Gly Val Ile Gly Cys Glu Phe Ala Ser Leu Phe His Thr Leu
             20                  25                  30

Gly Ser Glu Val Ser Val Ile Glu Ala Ser Ser Gln Ile Leu Ala Leu
         35                  40                  45

Asn Asn Pro Asp Ile Ser Lys Thr Met Phe Asp Lys Phe Thr Arg Gln
 50                  55                  60

Gly Leu Arg Phe Val Leu Glu Ala Ser Val Ser Asn Ile Glu Asp Ile
 65                  70                  75                  80

Gly Asp Arg Val Arg Leu Thr Ile Asn Gly Asn Val Glu Glu Tyr Asp
             85                  90                  95

Tyr Val Leu Val Ser Ile Gly Arg Arg Leu Asn Thr Glu Asn Ile Gly
            100                 105                 110

Leu Asp Lys Ala Gly Val Ile Cys Asp Glu Arg Gly Val Ile Pro Thr
        115                 120                 125

Asp Ala Thr Met Arg Thr Asn Val Pro Asn Ile Tyr Ala Ile Gly Asp
130                 135                 140

Ile Thr Gly Lys Trp Gln Leu Ala His Val Ala Ser His Gln Gly Ile
145                 150                 155                 160

Ile Ala Ala Arg Asn Ile Gly Gly His Lys Glu Ile Asp Tyr Ser
                165                 170                 175

Ala Val Pro Ser Val Ile Phe Thr Phe Pro Glu Val Ala Ser Val Gly
            180                 185                 190

Leu Ser Pro Thr Ala Ala Gln Gln His Leu Leu Leu Arg Leu Leu Phe
        195                 200                 205

Leu Lys Asn Leu Ile Gln Lys Lys Asn Ser Ser His Thr Cys Glu Glu
210                 215                 220

Glu Gly Val Trp Lys Thr Ser
225                 230
```

<210> SEQ ID NO 27
<211> LENGTH: 264
<212> TYPE: DNA
<213> ORGANISM: Chlamydia pneumoniae

<400> SEQUENCE: 27

```
atgagtcaaa aaaataaaaa ctctgctttt atgcatcccg tgaatatttc cacagattta    60
gcagttatag ttggcaaggg acctatgccc agaaccgaaa ttgtaaagaa agtttgggaa   120
tacattaaaa aacacaactg tcaggatcaa aaaaataaac gtaatatcct tcccgatgcg   180
aatcttgcca aagtctttgg ctctagtgat cctatcgaca tgttccaaat gaccaaagcc   240
ctttccaaac atattgtaaa ataa                                         264
```

<210> SEQ ID NO 28
<211> LENGTH: 87
<212> TYPE: PRT
<213> ORGANISM: Chlamydia pneumoniae

<400> SEQUENCE: 28

```
Met Ser Gln Lys Asn Lys Asn Ser Ala Phe Met His Pro Val Asn Ile
 1               5                  10                  15

Ser Thr Asp Leu Ala Val Ile Val Gly Lys Gly Pro Met Pro Arg Thr
                20                  25                  30

Glu Ile Val Lys Lys Val Trp Glu Tyr Ile Lys Lys His Asn Cys Gln
            35                  40                  45

Asp Gln Lys Asn Lys Arg Asn Ile Leu Pro Asp Ala Asn Leu Ala Lys
        50                  55                  60

Val Phe Gly Ser Ser Asp Pro Ile Asp Met Phe Gln Met Thr Lys Ala
65                  70                  75                  80

Leu Ser Lys His Ile Val Lys
                85
```

<210> SEQ ID NO 29
<211> LENGTH: 369
<212> TYPE: DNA
<213> ORGANISM: Chlamydia pneumoniae

<400> SEQUENCE: 29

```
atgccacgca tcattggaat tgatattcct gcaaagaaaa agttaaaaat aagtctgaca    60
tatatttatg gaataggatc agctcgttct gatgaaatca ttaaaaagtt gaagttagat   120
cctgaggcaa gagcctctga attaactgaa gaagaagtag gacgactgaa ctctctgcta   180
caatcagaat ataccgtaga agggatttg cgacgtcgtg ttcaatcgga tatcaaaaga   240
ttgatcgcca tccattctta tcgaggtcag agacatagac tttctttacc agtaagagga   300
caacgtacaa aaactaattc tcgtactcga aaggtaaaa gaaaaacagt cgcaggtaag   360
aagaaataa                                                          369
```

<210> SEQ ID NO 30
<211> LENGTH: 122
<212> TYPE: PRT
<213> ORGANISM: Chlamydia pneumoniae

<400> SEQUENCE: 30

```
Met Pro Arg Ile Ile Gly Ile Asp Ile Pro Ala Lys Lys Lys Leu Lys
 1               5                  10                  15

Ile Ser Leu Thr Tyr Ile Tyr Gly Ile Gly Ser Ala Arg Ser Asp Glu
                20                  25                  30

Ile Ile Lys Lys Leu Lys Leu Asp Pro Glu Ala Arg Ala Ser Glu Leu
            35                  40                  45

Thr Glu Glu Val Gly Arg Leu Asn Ser Leu Leu Gln Ser Glu Tyr
        50                  55                  60

Thr Val Glu Gly Asp Leu Arg Arg Arg Val Gln Ser Asp Ile Lys Arg
```

```
                65                  70                  75                  80
Leu Ile Ala Ile His Ser Tyr Arg Gly Gln Arg His Arg Leu Ser Leu
                    85                  90                  95
Pro Val Arg Gly Gln Arg Thr Lys Thr Asn Ser Arg Thr Arg Lys Gly
                100                 105                 110
Lys Arg Lys Thr Val Ala Gly Lys Lys Lys
        115                 120

<210> SEQ ID NO 31
<211> LENGTH: 10
<212> TYPE: PRT
<213> ORGANISM: Chlamydia trachomatis

<400> SEQUENCE: 31

Cys Ser Phe Ile Gly Gly Ile Thr Tyr Leu
1               5                   10

<210> SEQ ID NO 32
<211> LENGTH: 53
<212> TYPE: PRT
<213> ORGANISM: Chlamydia trachomatis

<400> SEQUENCE: 32

Leu Cys Val Ser His Lys Arg Arg Ala Ala Ala Val Cys Ser Phe
1               5                   10                  15

Ile Gly Gly Ile Thr Tyr Leu Ala Thr Phe Gly Ala Ile Arg Pro Ile
            20                  25                  30

Leu Phe Val Asn Lys Met Leu Ala Gln Pro Phe Leu Ser Ser Gln Thr
        35                  40                  45

Lys Ala Asn Met Gly
        50

<210> SEQ ID NO 33
<211> LENGTH: 161
<212> TYPE: DNA
<213> ORGANISM: Chlamydia trachomatis

<400> SEQUENCE: 33
atctttgtgt gtctcataag cgcagagcgg ctgcggctgt ctgtagcatc atcggaggaa      60
ttacctacct cgcgacattc ggagctatcc gtccgattct gtttgtcaac aaaatgctgg    120
caaaaccgtt tctttcttcc caaactaaag caaatatggg a                        161

<210> SEQ ID NO 34
<211> LENGTH: 53
<212> TYPE: PRT
<213> ORGANISM: Chlamydia trachomatis

<400> SEQUENCE: 34

Leu Cys Val Ser His Lys Arg Arg Ala Ala Ala Val Cys Ser Ile
1               5                   10                  15

Ile Gly Gly Ile Thr Tyr Leu Ala Thr Phe Gly Ala Ile Arg Pro Ile
            20                  25                  30

Leu Phe Val Asn Lys Met Leu Ala Lys Pro Phe Leu Ser Ser Gln Thr
        35                  40                  45

Lys Ala Asn Met Gly
        50

<210> SEQ ID NO 35
<211> LENGTH: 55
```

```
<212> TYPE: DNA
<213> ORGANISM: Chlamydia pneumoniae

<400> SEQUENCE: 35
gatatacata tgcatcacca tcaccatcac atgagtcaaa aaaaataaaa actct       55

<210> SEQ ID NO 36
<211> LENGTH: 33
<212> TYPE: DNA
<213> ORGANISM: Chlamydia pneumoniae

<400> SEQUENCE: 36
ctcgaggaat tcttatttta caatatgttt gga                               33

<210> SEQ ID NO 37
<211> LENGTH: 53
<212> TYPE: DNA
<213> ORGANISM: Chlamydia pneumoniae

<400> SEQUENCE: 37
gatatacata tgcatcacca tcaccatcac atgccacgca tcattggaat gat         53

<210> SEQ ID NO 38
<211> LENGTH: 30
<212> TYPE: DNA
<213> ORGANISM: Chlamydia pneumoniae

<400> SEQUENCE: 38
ctcgaggaat tcttatttct tcttacctgc                                   30

<210> SEQ ID NO 39
<211> LENGTH: 16
<212> TYPE: PRT
<213> ORGANISM: Artificial Sequence
<220> FEATURE:
<223> OTHER INFORMATION: Made in the lab

<400> SEQUENCE: 39

Lys Arg Asn Ile Asn Pro Asp Asp Lys Leu Ala Lys Val Phe Gly Thr
 1               5                  10                  15

<210> SEQ ID NO 40
<211> LENGTH: 16
<212> TYPE: PRT
<213> ORGANISM: Artificial Sequence
<220> FEATURE:
<223> OTHER INFORMATION: made in the lab

<400> SEQUENCE: 40

Lys Arg Asn Ile Leu Pro Asp Ala Asn Leu Ala Lys Val Phe Gly Ser
 1               5                  10                  15

<210> SEQ ID NO 41
<211> LENGTH: 15
<212> TYPE: PRT
<213> ORGANISM: Artificial Sequence
<220> FEATURE:
<223> OTHER INFORMATION: made in the lab

<400> SEQUENCE: 41

Lys Glu Tyr Ile Asn Gly Asp Lys Tyr Phe Gln Gln Ile Phe Asp
 1               5                  10                  15

<210> SEQ ID NO 42
<211> LENGTH: 16
```

```
<212> TYPE: PRT
<213> ORGANISM: Artificial Sequence
<220> FEATURE:
<223> OTHER INFORMATION: made in the lab

<400> SEQUENCE: 42

Lys Lys Ile Ile Ile Pro Asp Ser Lys Leu Gln Gly Val Ile Gly Ala
 1               5                  10                  15

<210> SEQ ID NO 43
<211> LENGTH: 15
<212> TYPE: PRT
<213> ORGANISM: Artificial Sequence
<220> FEATURE:
<223> OTHER INFORMATION: made in the lab

<400> SEQUENCE: 43

Lys Lys Leu Leu Val Pro Asp Asn Asn Leu Ala Thr Ile Ile Gly
 1               5                  10                  15

<210> SEQ ID NO 44
<211> LENGTH: 77
<212> TYPE: DNA
<213> ORGANISM: Artificial Sequence
<220> FEATURE:
<223> OTHER INFORMATION: Retroviral vector modified to contain Kozak
      translation inititation site and stop codons.

<400> SEQUENCE: 44
gatctgccgc caccatggaa ttcgatatcg gatccctgca gaagcttgag ctcgagcgcg    60
gccgctaatt agctgag                                                   77

<210> SEQ ID NO 45
<211> LENGTH: 77
<212> TYPE: DNA
<213> ORGANISM: Artificial Sequence
<220> FEATURE:
<223> OTHER INFORMATION: Retroviral vector modified to contain Kozak
      translation inititation site and stop codons.

<400> SEQUENCE: 45
acggcggtgg taccttaagc tatagcctag ggacgtcttc gaactcgagc tcgcgccggc    60
gattaatcga ctcagct                                                   77

<210> SEQ ID NO 46
<211> LENGTH: 78
<212> TYPE: DNA
<213> ORGANISM: Artificial Sequence
<220> FEATURE:
<223> OTHER INFORMATION: Retroviral vector modified to contain Kozak
      translation inititation site and stop codons.

<400> SEQUENCE: 46
gatctgccgc caccatggga attcgatatc ggatccctgc agaagcttga gctcgagcgc    60
ggccgctaat tagctgag                                                  78

<210> SEQ ID NO 47
<211> LENGTH: 78
<212> TYPE: DNA
<213> ORGANISM: Artificial Sequence
<220> FEATURE:
<223> OTHER INFORMATION: Retroviral vector modified to contain Kozak
      translation inititation site and stop codons.

<400> SEQUENCE: 47
```

-continued

```
acggcggtgg taccottaag ctatagccta gggacgtctt cgaactcgag ctcgcgccgg       60
cgattaatcg actcagct                                                     78

<210> SEQ ID NO 48
<211> LENGTH: 79
<212> TYPE: DNA
<213> ORGANISM: Artificial Sequence
<220> FEATURE:
<223> OTHER INFORMATION: Retroviral vector modified to contain Kozak
      translation inititation site and stop codons.

<400> SEQUENCE: 48
gatctgccgc caccatgggg aattcgatat cggatccctg cagaagcttg agctcgagcg       60
cggccgctaa ttagctgag                                                    79

<210> SEQ ID NO 49
<211> LENGTH: 79
<212> TYPE: DNA
<213> ORGANISM: Artificial Sequence
<220> FEATURE:
<223> OTHER INFORMATION: Retroviral vector modified to contain Kozak
      translation inititation site and stop codons.

<400> SEQUENCE: 49
acggcggtgg tacccttaa gctatagcct agggacgtct tcgaactcga gctcgcgccg        60
gcgattaatc gactcagct                                                    79
```